United States Patent
Tracey et al.

(10) Patent No.: US 7,632,080 B2
(45) Date of Patent: Dec. 15, 2009

(54) BEZEL ASSEMBLY FOR PNEUMATIC CONTROL

(75) Inventors: Brian Tracey, Litchfield, NH (US); David W. McGill, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 475 days.

(21) Appl. No.: 10/697,450

(22) Filed: Oct. 30, 2003

(65) Prior Publication Data

US 2005/0095154 A1 May 5, 2005

(51) Int. Cl.
 *F04B 43/12* (2006.01)
(52) U.S. Cl. ............... 417/477.9; 417/395; 417/413.1; 417/477.2; 92/98 R
(58) Field of Classification Search .......... 417/477.9, 417/477.12, 477.13, 477.14, 384, 389, 395, 417/413.1, 480, 477.2; 92/98 R; 604/141
See application file for complete search history.

(56) References Cited

U.S. PATENT DOCUMENTS

| | | | |
|---|---|---|---|
| 1,133,254 A | 3/1915 | Backus | |
| 1,664,576 A | 4/1928 | Stuart et al. | |
| 1,792,906 A | 2/1931 | Heilos | 251/209 |
| 2,313,551 A | 3/1943 | Hurlbut | 417/387 |
| 2,525,251 A | 10/1950 | Willard | 449/17 |
| 2,526,017 A | 10/1950 | Figg | 251/209 |
| 2,703,055 A | 3/1955 | Veth et al. | 417/205 |
| 2,776,854 A | 1/1957 | Billstrom | 292/256 |
| 2,834,504 A | 5/1958 | Joseph | 220/211 |
| 2,902,253 A | 9/1959 | Page | 251/209 |
| 3,048,121 A | 8/1962 | Sheesley | 417/394 |
| 3,339,956 A | 9/1967 | Bencene | 292/127 |
| 3,372,501 A * | 3/1968 | Greene | 40/450 |
| 3,449,864 A | 6/1969 | Prost-Dame et al. | 49/477.1 |
| 3,481,076 A | 12/1969 | Bedard | 49/279 |

(Continued)

FOREIGN PATENT DOCUMENTS

WO        WO 87/06119        10/1987

(Continued)

OTHER PUBLICATIONS

"bezel." Dictionary.com Unabridged (v 1.1). Random House, Inc. Jan. 28, 2008. <Dictionary.com http://dictionary.reference.com/browse/bezel>.*

(Continued)

*Primary Examiner*—Devon C Kramer
*Assistant Examiner*—Leonard J Weinstein
(74) *Attorney, Agent, or Firm*—Marc J Gorayeb

(57) ABSTRACT

A bezel and bezel assembly in which the bezel is a rigid block with a plurality of cavities. A depression in the block has ribs extending up therefrom to form an elevated contour. The depression includes at least one cavity therein for the application of air pressure into the depression and over the elevated contour. A gasket fits over the bezel so that positive pressure applied through the at least one cavity in the depression forces a gasket membrane to expand away from the pumping side and negative pressure applied through the at least one cavity in the depression pulls the gasket membrane against the elevated contour of the ribs. The bezel may include solvent bondable tubing connections for making pneumatic connections to the bezel.

55 Claims, 22 Drawing Sheets

U.S. PATENT DOCUMENTS

| | | | |
|---|---|---|---|
| 3,540,694 A | 11/1970 | Cornelius | 251/209 |
| 3,570,486 A | 3/1971 | Engelsher et al. | 128/218 |
| 3,722,858 A | 3/1973 | Sugimoto et al. | 251/209 |
| 3,727,882 A | 4/1973 | Burris et al. | 251/209 |
| 3,814,548 A | 6/1974 | Rupp | 417/395 |
| 3,856,338 A | 12/1974 | Johnsson | 292/256 |
| 4,072,934 A | 2/1978 | Hiller et al. | 340/243 |
| 4,073,521 A | 2/1978 | Mena | 292/256.65 |
| 4,093,176 A | 6/1978 | Contastin | 249/167 |
| 4,096,211 A | 6/1978 | Rameau | |
| 4,161,264 A | 7/1979 | Malmgren et al. | 222/135 |
| 4,212,589 A | 7/1980 | Bosio | 417/12 |
| 4,230,300 A | 10/1980 | Wiltse | 251/205 |
| 4,247,018 A | 1/1981 | Credle | 222/1 |
| 4,431,425 A | 2/1984 | Thompson et al. | 604/246 |
| 4,468,219 A | 8/1984 | George et al. | 604/67 |
| 4,479,760 A | 10/1984 | Bilstad et al. | 417/375 |
| 4,479,761 A | 10/1984 | Bilstad et al. | 417/395 |
| 4,479,762 A | 10/1984 | Bilstad et al. | 417/395 |
| 4,576,211 A | 3/1986 | Valentini et al. | 141/329 |
| 4,623,450 A | 11/1986 | Vantard et al. | |
| 4,634,430 A | 1/1987 | Polaschegg | 604/141 |
| 4,648,868 A | 3/1987 | Hardwick et al. | 604/32 |
| 4,650,339 A | 3/1987 | Chetcuti et al. | 366/142 |
| 4,662,540 A | 5/1987 | Schroter | 222/55 |
| 4,662,829 A | 5/1987 | Nehring | 417/395 |
| 4,667,927 A | 5/1987 | Oscarsson | 251/209 |
| 4,696,671 A | 9/1987 | Epstein et al. | 604/67 |
| 4,698,160 A | 10/1987 | Haraguchi | 210/647 |
| 4,718,447 A | 1/1988 | Marshall | 137/268 |
| 4,721,138 A | 1/1988 | Simonazzi | 141/150 |
| 4,778,451 A | 10/1988 | Kamen | 604/67 |
| 4,798,580 A | 1/1989 | DeMeo et al. | 604/30 |
| 4,804,366 A | 2/1989 | Zdeb et al. | 604/85 |
| 4,807,660 A | 2/1989 | Aslanian | 137/382 |
| 4,808,161 A | 2/1989 | Kamen | 604/67 |
| 4,818,186 A | 4/1989 | Pastrone et al. | 417/63 |
| 4,826,482 A | 5/1989 | Kamen | 604/67 |
| 4,828,543 A | 5/1989 | Weiss et al. | 604/609 |
| 4,833,922 A | 5/1989 | Frick et al. | 73/756 |
| 4,850,978 A | 7/1989 | Dudar et al. | 604/201 |
| 4,855,714 A | 8/1989 | Clarkson et al. | 340/521 |
| 4,925,444 A | 5/1990 | Orkin et al. | 604/250 |
| 4,927,198 A | 5/1990 | Fennell et al. | 292/306 |
| 4,976,162 A | 12/1990 | Kamen | 73/865.9 |
| 5,005,604 A | 4/1991 | Aslanian | 137/556 |
| 5,006,050 A | 4/1991 | Cooke et al. | 417/478 |
| 5,045,068 A | 9/1991 | Kawai et al. | 604/246 |
| 5,051,922 A | 9/1991 | Toral et al. | 364/510 |
| 5,062,774 A | 11/1991 | Kramer et al. | 417/413 |
| 5,069,792 A | 12/1991 | Prince et al. | 210/627 |
| 5,088,515 A | 2/1992 | Kamen | 137/15 |
| 5,088,901 A * | 2/1992 | Brauer | 417/386 |
| 5,098,262 A | 3/1992 | Wecker et al. | 417/479 |
| 5,098,371 A | 3/1992 | Juji et al. | 604/4 |
| 5,113,904 A | 5/1992 | Aslanian | 137/556 |
| 5,116,316 A | 5/1992 | Sertic et al. | 604/83 |
| 5,122,116 A | 6/1992 | Kriesel et al. | 604/89 |
| 5,146,414 A | 9/1992 | McKown et al. | 364/510 |
| 5,150,796 A | 9/1992 | Pierson | 209/370 |
| 5,156,186 A | 10/1992 | Manska | 137/556 |
| 5,167,837 A | 12/1992 | Snodgrass et al. | 210/767 |
| 5,178,182 A | 1/1993 | Kamen | 137/454.2 |
| 5,186,333 A | 2/1993 | Pierson et al. | 209/370 |
| 5,197,787 A | 3/1993 | Matsuda et al. | 303/10 |
| 5,255,072 A | 10/1993 | Mikasa et al. | 356/432 |
| 5,267,956 A | 12/1993 | Beuchat | 604/30 |
| 5,272,646 A | 12/1993 | Farmer | 364/509 |
| 5,279,504 A | 1/1994 | Williams | 417/395 |
| 5,290,076 A | 3/1994 | Smith | 292/25 |
| 5,292,306 A | 3/1994 | Wynkoop et al. | 604/51 |
| 5,294,157 A | 3/1994 | Smith et al. | 292/25 |
| 5,302,093 A | 4/1994 | Owens et al. | 417/474 |
| 5,325,884 A | 7/1994 | Mirel et al. | 137/110 |
| 5,330,426 A | 7/1994 | Kriesel et al. | 604/89 |
| 5,336,053 A | 8/1994 | Wynkoop | 417/53 |
| D350,823 S | 9/1994 | Lanigan | D24/111 |
| 5,350,357 A | 9/1994 | Kamen et al. | 604/29 |
| 5,351,686 A | 10/1994 | Steuer et al. | 600/310 |
| 5,355,890 A | 10/1994 | Aguirre et al. | 128/680 |
| 5,378,126 A | 1/1995 | Abrahamson et al. | 417/479 |
| 5,384,714 A | 1/1995 | Kidd | 702/51 |
| 5,385,540 A | 1/1995 | Abbott et al. | 604/4 |
| 5,401,059 A | 3/1995 | Ferrario | 283/67 |
| 5,408,420 A | 4/1995 | Slocum et al. | 702/51 |
| 5,411,472 A | 5/1995 | Steg et al. | 604/4 |
| 5,421,823 A | 6/1995 | Kamen et al. | 604/28 |
| 5,423,738 A | 6/1995 | Robinson et al. | 604/601 |
| 5,428,527 A | 6/1995 | Niemi | 364/152 |
| 5,429,485 A | 7/1995 | Dodge | 417/442 |
| 5,431,626 A | 7/1995 | Bryant et al. | 604/65 |
| 5,438,510 A | 8/1995 | Bryant et al. | 364/413.11 |
| 5,439,355 A | 8/1995 | Jimison et al. | 417/63 |
| 5,463,228 A | 10/1995 | Krause | 250/577 |
| 5,474,683 A | 12/1995 | Bryant et al. | 210/646 |
| 5,478,337 A | 12/1995 | Okamoto et al. | 604/413 |
| 5,482,440 A | 1/1996 | Dennehey et al. | 417/63 |
| 5,558,255 A | 9/1996 | Sancoff et al. | 222/189.06 |
| 5,575,310 A | 11/1996 | Kamen et al. | 137/614.11 |
| 5,578,012 A | 11/1996 | Kamen et al. | 604/151 |
| 5,579,244 A | 11/1996 | Brown | 364/558 |
| 5,584,671 A | 12/1996 | Schweitzer, Jr. et al. | 417/298 |
| 5,588,816 A | 12/1996 | Abbott et al. | 417/479 |
| 5,593,290 A | 1/1997 | Greisch et al. | 417/478 |
| 5,628,908 A * | 5/1997 | Kamen et al. | 210/646 |
| 5,634,896 A | 6/1997 | Bryant et al. | 604/29 |
| 5,638,737 A * | 6/1997 | Mattson et al. | 92/101 |
| 5,647,391 A | 7/1997 | Chan et al. | 366/152.4 |
| 5,649,810 A | 7/1997 | Schweitzer, Jr. et al. | 417/298 |
| 5,651,775 A | 7/1997 | Walker et al. | 604/207 |
| 5,681,285 A | 10/1997 | Ford et al. | 604/151 |
| 5,713,865 A | 2/1998 | Manning et al. | 604/122 |
| 5,716,343 A | 2/1998 | Kriesel et al. | 604/132 |
| 5,755,683 A | 5/1998 | Houle et al. | 604/30 |
| 5,776,103 A | 7/1998 | Kriesel et al. | 604/132 |
| 5,795,328 A | 8/1998 | Barnitz et al. | 604/67 |
| 5,808,181 A | 9/1998 | Wamsiedler et al. | 210/646 |
| 5,816,779 A | 10/1998 | Lawless et al. | 417/63 |
| 5,823,026 A | 10/1998 | Finke | 70/276 |
| 5,837,905 A | 11/1998 | Strauss et al. | 73/861.63 |
| 5,868,162 A | 2/1999 | Dickerson, Jr. | 137/557 |
| 5,879,328 A | 3/1999 | Holmberg et al. | 604/82 |
| 5,883,299 A | 3/1999 | Green et al. | 417/63 |
| 5,935,105 A | 8/1999 | Manning et al. | 604/122 |
| 5,938,634 A | 8/1999 | Packard | 604/29 |
| 5,965,821 A | 10/1999 | Grudzien | 73/724 |
| 5,989,423 A | 11/1999 | Kamen et al. | 210/258 |
| 6,022,483 A | 2/2000 | Aral | 216/59 |
| 6,041,801 A | 3/2000 | Gray et al. | 137/14 |
| 6,065,941 A | 5/2000 | Gray et al. | 417/63 |
| 6,070,761 A | 6/2000 | Bloom et al. | 222/81 |
| 6,109,881 A * | 8/2000 | Snodgrass et al. | 417/53 |
| 6,136,586 A | 10/2000 | Budowsky | 435/238 |
| 6,210,361 B1 | 4/2001 | Kamen et al. | 604/82 |
| 6,223,130 B1 | 4/2001 | Gray et al. | 702/51 |
| 6,234,997 B1 | 5/2001 | Kamen et al. | 604/131 |
| 6,245,570 B1 | 6/2001 | Grimm et al. | 436/55 |
| 6,264,458 B1 | 7/2001 | Marcuz et al. | 425/451.9 |
| 6,302,653 B1 | 10/2001 | Bryant et al. | |
| 6,343,614 B1 | 2/2002 | Gray et al. | 137/14 |
| 6,364,857 B1 | 4/2002 | Gray et al. | 604/153 |
| 6,382,923 B1 * | 5/2002 | Gray | 417/53 |
| 6,416,293 B1 | 7/2002 | Bouchard et al. | 417/53 |
| 6,464,667 B1 | 10/2002 | Kamen et al. | 604/131 |

| | | | | | | |
|---|---|---|---|---|---|---|
| 6,485,263 | B1 | 11/2002 | Bryant et al. ................. 417/53 | WO | WO 99/10028 | 3/1999 |
| 6,503,062 | B1 | 1/2003 | Gray et al. .................... 417/53 | WO | WO 01/18396 A1 | 3/2001 |
| 6,520,747 | B2 | 2/2003 | Gray et al. .................... 417/63 | WO | WO 03/086509 A1 | 10/2003 |
| 6,527,758 | B2 | 3/2003 | Ko ............................. 604/411 | | | |
| 6,604,908 | B1 | 8/2003 | Bryant et al. ................. 417/26 | | | |
| 6,663,359 | B2 | 12/2003 | Gray et al. .................. 417/383 | | | |
| 6,709,417 | B1 | 3/2004 | Houle et al. | | | |
| 6,726,656 | B2 | 4/2004 | Kamen et al. | | | |
| 6,749,403 | B2 | 6/2004 | Bryant et al. | | | |
| 6,790,014 | B2 * | 9/2004 | Bowen ....................... 417/392 | | | |
| 6,877,713 | B1 | 4/2005 | Gray et al. | | | |
| 7,011,742 | B2 | 3/2006 | Rosiello .................... 210/109 | | | |
| 2003/0229302 | A1 * | 12/2003 | Robinson et al. ........... 604/4.01 | | | |
| 2004/0054251 | A1 * | 3/2004 | Liotta .......................... 600/17 | | | |
| 2004/0091374 | A1 | 5/2004 | Gray | | | |
| 2005/0230292 | A1 | 10/2005 | Beden et al. | | | |

FOREIGN PATENT DOCUMENTS

WO      WO 94/22566      10/1994

OTHER PUBLICATIONS

Authorized Officer Ellen Elskamp, *The International Search Report and the Written Opinion of the International Searching Authority*, International Searching Authority, Jun. 14, 2005, 21 pages.

Authorized Officer Ellen Elskamp, *The International Search Report and the Written Opinion of the International Searching Authority*, International Searching Authority, Apr. 4, 2005, 13 pages.

Authorized Officer Ellen Elskamp, *Invitation to Pay Additional Fees /Communication Relating to the Results of the Partial International Search*, International Searching Authority, May 3, 2005, 7 pages.

* cited by examiner

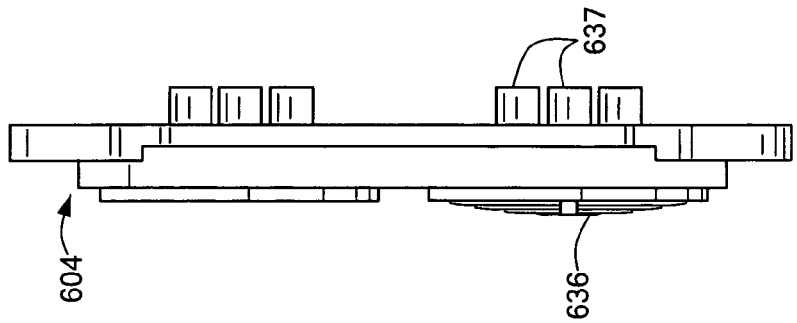
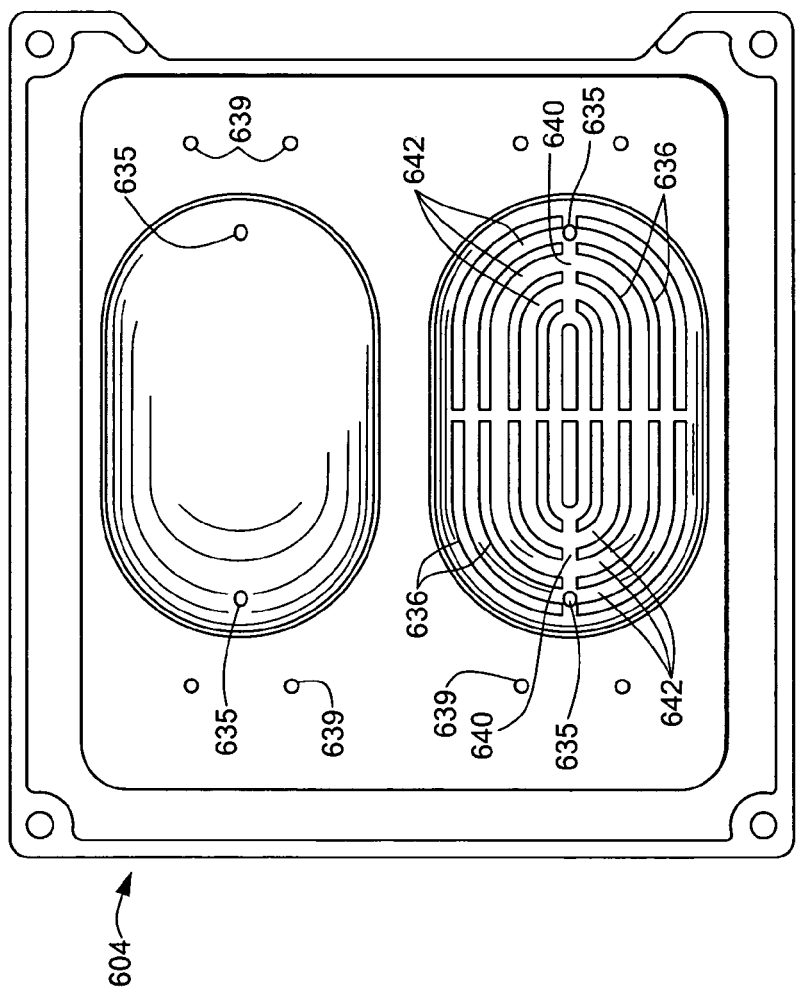 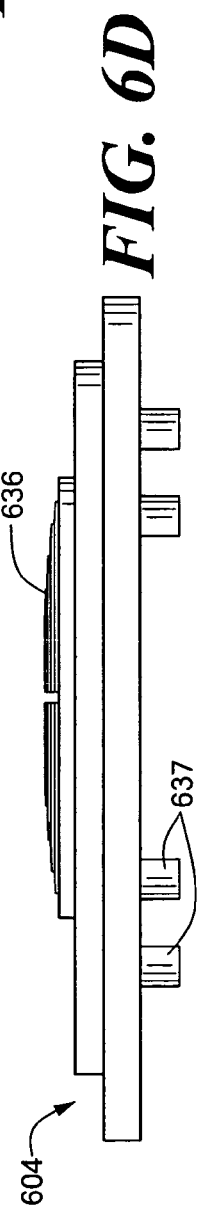
FIG. 6E
FIG. 6D
FIG. 6C

BEZEL ASSEMBLY FOR PNEUMATIC CONTROL

CROSS-REFERENCE TO RELATED APPLICATION(S)

The present application may include subject matter related to one or more of the following commonly-owned United States patent applications, each of which was filed on even date herewith and is hereby incorporated herein by reference in its entirety:

U.S. patent application Ser. No. 10/696,969 entitled SYSTEM, DEVICE, AND METHOD FOR MIXING A SUBSTANCE WITH A LIQUID (referred to herein as "Application D70");

U.S. patent application Ser. No. 10/696,893 entitled SYSTEM, DEVICE, AND METHOD FOR MIXING LIQUIDS (referred to herein as "Application D71");

U.S. patent application Ser. No. 10/696,818 entitled TWO-STAGE MIXING SYSTEM, APPARATUS, AND METHOD (referred to herein as "Application D72");

U.S. patent application Ser. No. 10/697,176 entitled SYSTEM AND METHOD FOR PUMPING FLUID USING A PUMP CASSETTE (referred to herein as "Application D73");

U.S. patent application Ser. No. 10/696,984 entitled DOOR LOCKING MECHANISM (referred to herein as "Application D74");

U.S. patent application Ser. No. 10/697,862 entitled PUMP CASSETTE WITH SPIKING ASSEMBLY (referred to herein as "Application D84"); and U.S. patent application Ser. No. 10/696,990 entitled PUMP CASSETTE BANK (referred to herein as "Application D85").

FIELD OF THE INVENTION

The present invention relates generally to pneumatically controlled pumps.

BACKGROUND OF THE INVENTION

Millions of people receive blood transfusions each year. Although helpful in many cases, blood transfusions have associated risks. Among others, there is a risk that microorganisms capable of causing disease (i.e., pathogens) could pass from the donor blood to the ultimate blood recipient. For example, untreated blood used in a blood transfusion could have pathogens causing the West Nile Virus, or AIDS. It thus is critical for the public health to ensure that transfused blood is substantially free of pathogens.

The medical community has responded to this need by developing various techniques for removing known and unknown pathogens from donated blood. One technique involves mixing precise amounts of a diluted anti-pathogen compound with blood. Some time after mixing, a rinsing process removes the anti-pathogen compound from the blood. One complexity with this process, however, is the fact that the diluted anti-pathogen compound has a very short shelf life (e.g., on the order of about four hours). Accordingly, the diluted anti-pathogen compound must be produced a relatively short time before it is mixed with blood.

The anti-pathogen compound is not easy to handle before it is diluted. To the contrary, it has a very high pH (e.g., on the order of 11.0 or higher) and thus, is highly caustic and toxic. Mere contact with the undiluted solution can melt plastic, or burn flesh. Because of these undesirable properties, the undiluted solution typically is manually diluted by highly trained laboratory technicians that necessarily must be protected from direct contact with it. Consequently, laboratory technicians often are required to wear relatively impermeable protective gear while diluting the solution behind a chemical laminar flowhood. Such a process, however, is inherently slow, imprecise, and costly due to the multitude of safety requirements. Moreover, even with safeguards, diluting the undiluted solution still poses a risk to the laboratory technician.

SUMMARY OF THE INVENTION

In connection with developing a pneumatically operated pump cassette with pneumatically operated pump chambers and valves for use in diluting anti-pathogen compound and mixing diluted anti-pathogen compound with blood, a new bezel and associated equipment was invented. In accordance with one aspect of the invention, the bezel is formed by a rigid block having a plurality of cavities on a pumping side of the block. A first depression in the pumping side of the block has at least one of the cavities therein. Ribs either integral to the block or coupled to the block extend up from the depression to form an elevated contour. The ribs allow pneumatic pressure applied through the at least one cavity in the depression to be applied over the elevated contour. A bezel assembly further includes a gasket that fits over the pumping side of the bezel. Positive pressure through the cavity in the depression forces the gasket away from the pumping side and negative pressure through the cavity pulls the gasket against the elevated contour of the ribs.

The elevated contour limits the movement of the gasket into the depression thus reducing the pump stroke. The elevated contour may be in the shape of a mound that increases in height from a perimeter of the depression toward a higher middle of the mound. In accordance with a further aspect of the invention, the ribs extend up from a chamber wall of the depression. Thus, removal of the ribs by milling, or otherwise, leaves an open chamber defined by the chamber wall for delivering a larger pump stroke.

The ribs of an embodiment of the invention, may be arranged to provide a symmetrical grid of air passages. The air passages may be in fluid communication with two cavities in the depression. A further embodiment of the invention may provide the bezel with a second depression. The second depression may be constructed with or without ribs.

In order to provide air pressures through the cavities of the bezel, ports in fluid communication with the cavities are accessible from the back side of the rigid block. In particular embodiments, the ports are hollow tubular structures integral with the rigid block. Further, the inner diameter of a port may be larger in size than the cavity in fluid communication therewith. The ports may provide solvent bondable tubing connections to the bezel.

BRIEF DESCRIPTION OF THE DRAWINGS

In the accompanying drawings:

FIG. 6C shows a plan view of the bezel of FIG. 6B.

FIG. 6D shows a side view of the bezel of FIG. 6B.

FIG. 6E shows an end view of the bezel of FIG. 6B.

DETAILED DESCRIPTION OF A PREFERRED EMBODIMENT

In order to mix two liquids, a first liquid is pumped into a first pump chamber of a pumping apparatus through a channel of the pumping apparatus. A second liquid is pumped from a second pump chamber of the pumping apparatus into either the channel or the first pump chamber, preferably while the first liquid is being pumped into the first pump chamber. In this way, the two liquids are mixed within the pumping apparatus, and, more specifically, within the channel and/or the first pump chamber of the pumping apparatus. The second liquid is preferably pumped in a pulsatile mode in which small quantities of the second liquid are pumped at intervals. The quantity and/or the interval can be dynamically adjusted to result in a predetermined concentration of the two liquids. The contents of the first pump chamber are pumped to a receptacle.

The pumping apparatus may be a disposable pump cassette. The pump cassette typically includes two pump chambers and various valves. The pump chambers and valves are preferably operated pneumatically.

In exemplary embodiments, an anti-pathogen solution is mixed with a red blood cell concentrate (RBCC) to form an incubation solution for reducing pathogens in the RBCC. The anti-pathogen solution is prepared by mixing a caustic anti-pathogen compound known as PEN110™ or INACTINE™, which is an organic solvent with a pH over 11 that is distributed by V.I. Technologies, Inc. of Watertown, Mass., with a buffer solution of sodium phosphate to a predetermined concentration (e.g., 1 part anti-pathogen compound to 99 parts buffer solution), preferably as described in Application D70. For convenience, this mixing of anti-pathogen compound with buffer solution may be referred to hereinafter as "compounding," and an apparatus that performs such compounding may be referred to hereinafter as a "compounder" or "compounder pump." The incubation solution is prepared by mixing the anti-pathogen solution with the RBCC to a predetermined concentration (e.g., 1 part anti-pathogen solution to 9 parts RBCC), as described below. For convenience, this mixing of anti-pathogen solution with RBCC may be referred to hereinafter as "blood processing," and an apparatus that performs such blood processing may be referred to hereinafter as a "blood pump."

System Overview

Figure 1A:
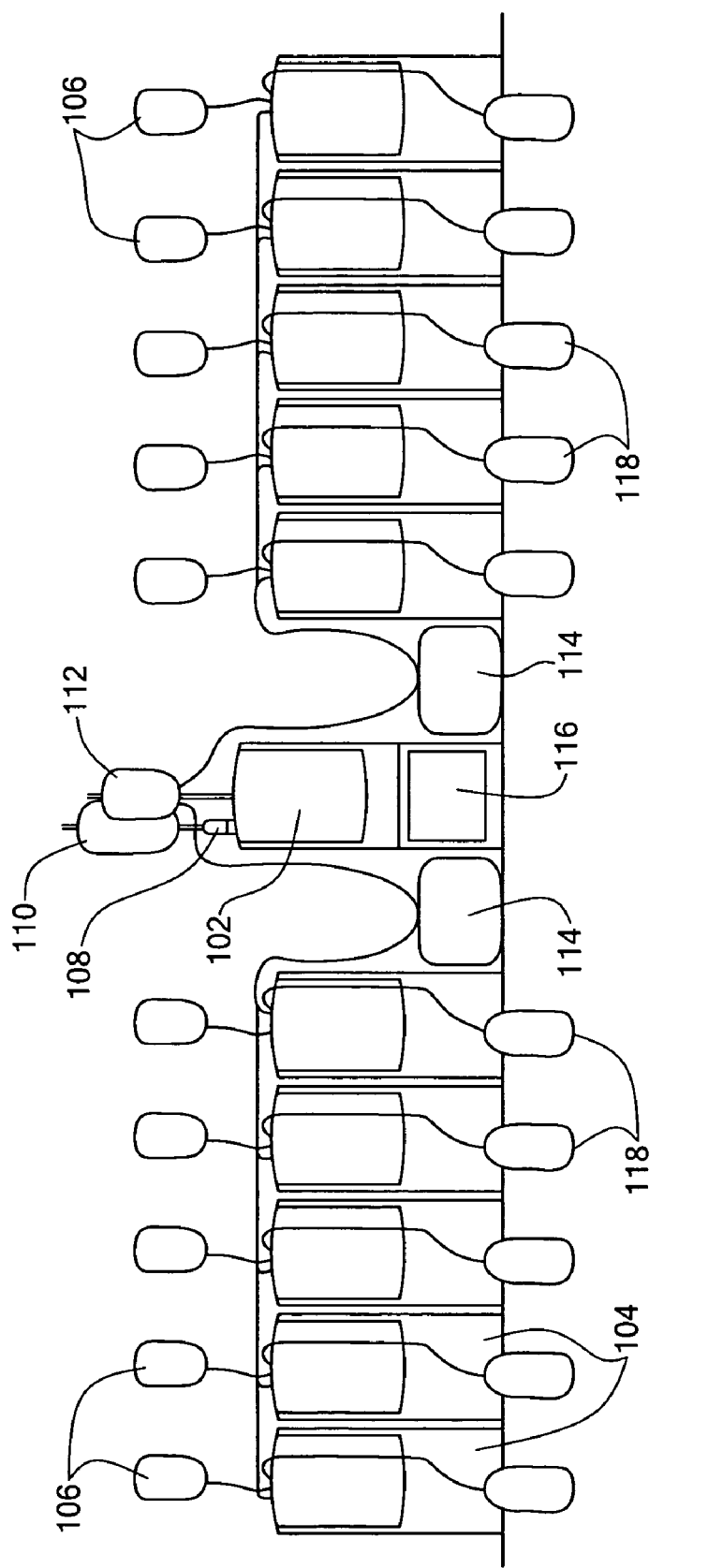
FIG. 1A shows an exemplary blood processing system having a plurality of blood pumps.

FIG. 1A shows an exemplary blood processing system 100 having a plurality of blood pumps. Among other things, the blood processing system 100 includes a single compounder pump 102 and ten essentially identical blood pumps 104 organized as two banks of five blood pumps each. The compounder pump 102 pumps buffer solution from a buffer solution container 110 into a vial of anti-pathogen compound 108. The mixture, referred to as a working solution, is pumped into a working solution container 112. Each of the blood pumps 104 mixes working solution from the working solution container 112 with red blood cell concentrate (RBCC) from a RBCC container 106 to form an incubation solution that is pumped into an incubation bag 118. The incubation solution is typically allowed to incubate for some period of time, after which it is rinsed to remove the anti-pathogen compound to produce a pathogen reduced blood product. The blood processing system 100 typically also includes two sterile docks 114 that are used by the operator to splice together plastic tubing as necessary for various blood processing operations. The blood processing system 100 is controlled through a user interface 116.

Figure 1B:
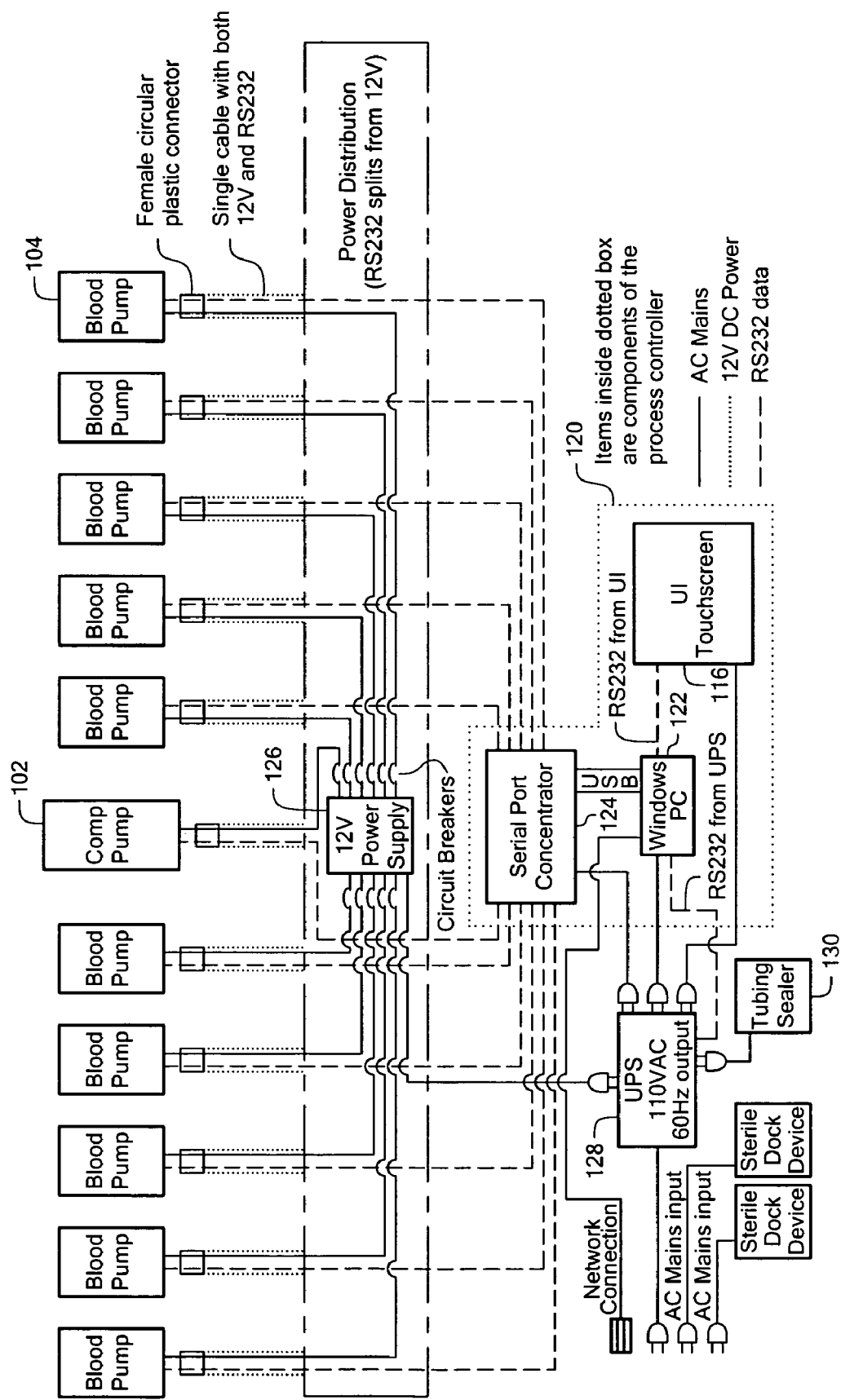
FIG. 1B shows an exemplary wiring diagram for one embodiment of the blood processing system shown in FIG. 1A.

FIG. 1B shows an exemplary wiring diagram for one embodiment of the blood processing system 100. The compounder pump 102 and the blood pumps 104 are typically powered from a common 12-Volt external power supply 126, and are controlled by an external process controller 120. The process controller 120 includes the user interface 116, a computer 122, and a serial port concentrator 124. The compounder pump 102 and the blood pumps 104 are in communication with the process controller 120 through the serial port concentrator 124, for example, over RS-232 communication links. The blood processing system 100 typically includes a tubing sealer 130 for sealing plastic tubing as necessary for various blood processing operations. The blood processing system 100 typically includes an uninterruptible power supply (UPS) 128 for maintaining electrical power to the 12-Volt power supply, the process controller, and other components in the event of a primary power loss.

Figure 1C:
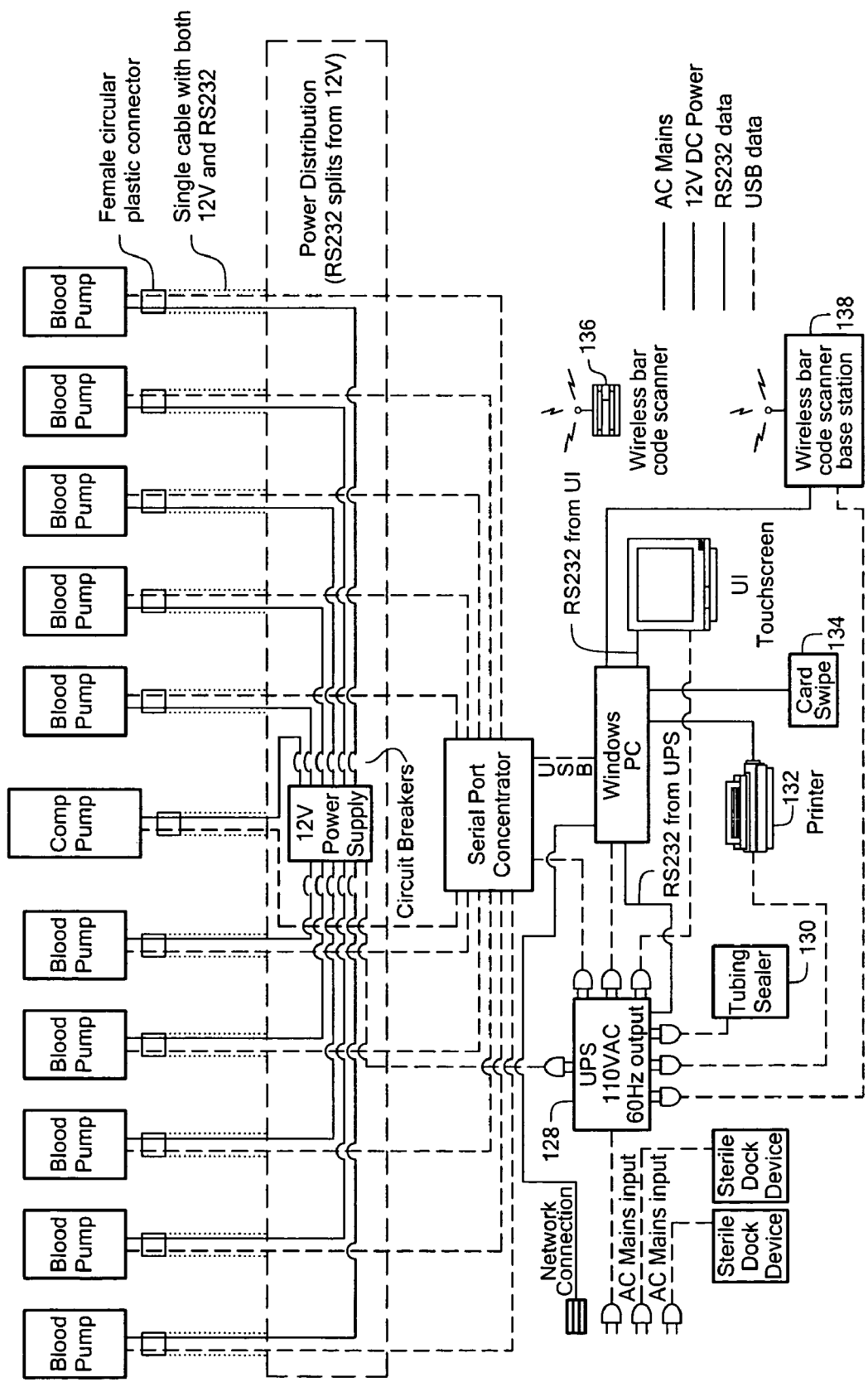
FIG. 1C shows an exemplary wiring diagram for another embodiment of the blood processing system shown in FIG. 1A.

FIG. 1C shows an exemplary wiring diagram for another embodiment of the blood processing system 100. The blood processing system 100 may include a printer in communication with the process controller for printing out reports. The blood processing system 100 may include a card reader 134 in communication with the process controller for card-based operator identification. The blood processing system 100 may include a wireless bar code scanner base station 138 in communication with the process controller for receiving bar code information scanned using a wireless bar code scanner 136. Bar codes are typically used to track the various solution containers and the pumps on which those containers were processed.

The process controller 120 coordinates the actions of the compounder pump 102, the blood pumps 104, and the operator throughout the various mixing operations, as described in greater detail in Application D72. The process controller 120 initiates high level embedded commands within the pumps to move and mix the fluids. The process controller 120 instructs the operator through the setup and teardown of each process through the user interface 116. The user interface 116 is also used to inform the operator of any anomalies that may occur during mixing operations.

When the blood processing system 100 is operating from the uninterruptible power supply 128 and at other appropriate times, the process controller 120 will prevent compounding and other pump operations from starting, although the pumps will generally be allowed to complete any ongoing operations. Furthermore, if the process controller fails, the pumps have internal logic for safely completing or terminating any ongoing operations.

Blood Disposables

The process controller 120 coordinates blood processing for an entire bank of five blood pumps 104 at a time. Specifically, five pump cassettes, each connected to a RBCC container and an incubation bag for receiving the incubation solution, are loaded respectively into the five blood pumps 104. The five pump cassettes are preferably connected by a single working solution inlet tube to the working solution container so that all five blood pumps draw working solution from the single working solution container.

For convenience, the five interconnected pump cassettes along with their respective incubation bags and various plastic tubing may be referred to hereinafter as a "blood disposables set." The blood disposables set is preferably used for a single blood processing cycle and is then discarded. The blood disposables set is described in greater detail in Application D85.

Figure 2:
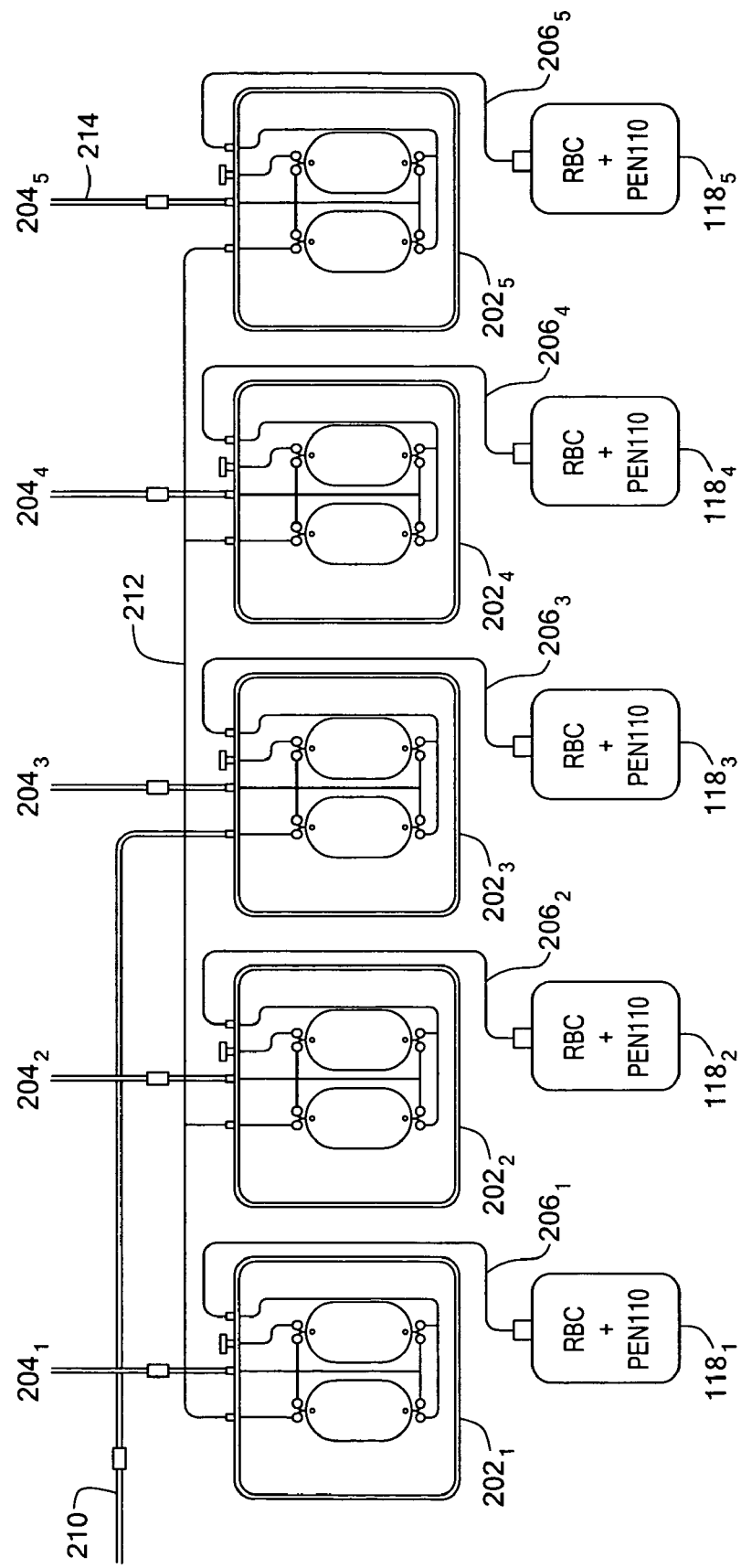
FIG. 2 shows an exemplary blood disposables set.

FIG. 2 shows an exemplary blood disposables set 200. The blood disposables set 200 includes five pump cassettes $202_{1-5}$, each respectively having a RBCC inlet tube $204_{1-5}$ connected to an RBC inlet port of the pump cassette and an incubation solution outlet tube $206_{1-5}$ connected to an outlet port of the pump cassette and to an incubation bag $118_{1-5}$. The blood disposables set 200 also includes working solution distribution tubing 212 that connects to a working solution inlet port on each pump cassette $202_{1-5}$ and to a single working solution inlet tube 210 so that the working solution inlet ports of all pump cassettes $202_{1-5}$ are effectively connected to the single working solution inlet tube 210. The working solution inlet tube 210 preferably connects to the working solution distribution tubing 212 close to where the working solution inlet port of the middle pump cassette $202_3$ connects to the tubing 212, and the working solution inlet ports of each concentric pair of pump cassettes is preferably connected to the tubing 212 a substantially equal distance from that center connection such that the working solution inlet ports of the pump cassettes $202_1$ and $202_5$ are essentially equidistant from the center connection and the working solution inlet ports of the pump cassettes $202_2$ and $202_4$ are essentially equidistant from the center connection. Among other things, this spacing of pump cassettes along the tubing 212 facilitates priming of the pumps, as discussed below. In order to perform blood processing, each RBCC inlet tube 204 is connected to a separate RBCC container 106, and the working solution inlet tube 210 is connected to the common working solution container 112. The blood disposables set 200 also includes six break-away closures 214, one on each of the RBCC inlet tubes 204 and one on the working solution inlet tube 210. In order to reduce the likelihood of confusing which RBCC bag and which incubation bag is associated with each pump cassette, the RBCC inlet tubes 204 and the incubation solution outlet tubes 206 are preferably coded, for example, by alternating between color-striped and clear tubing from cassette to cassette.

Figure 3A:
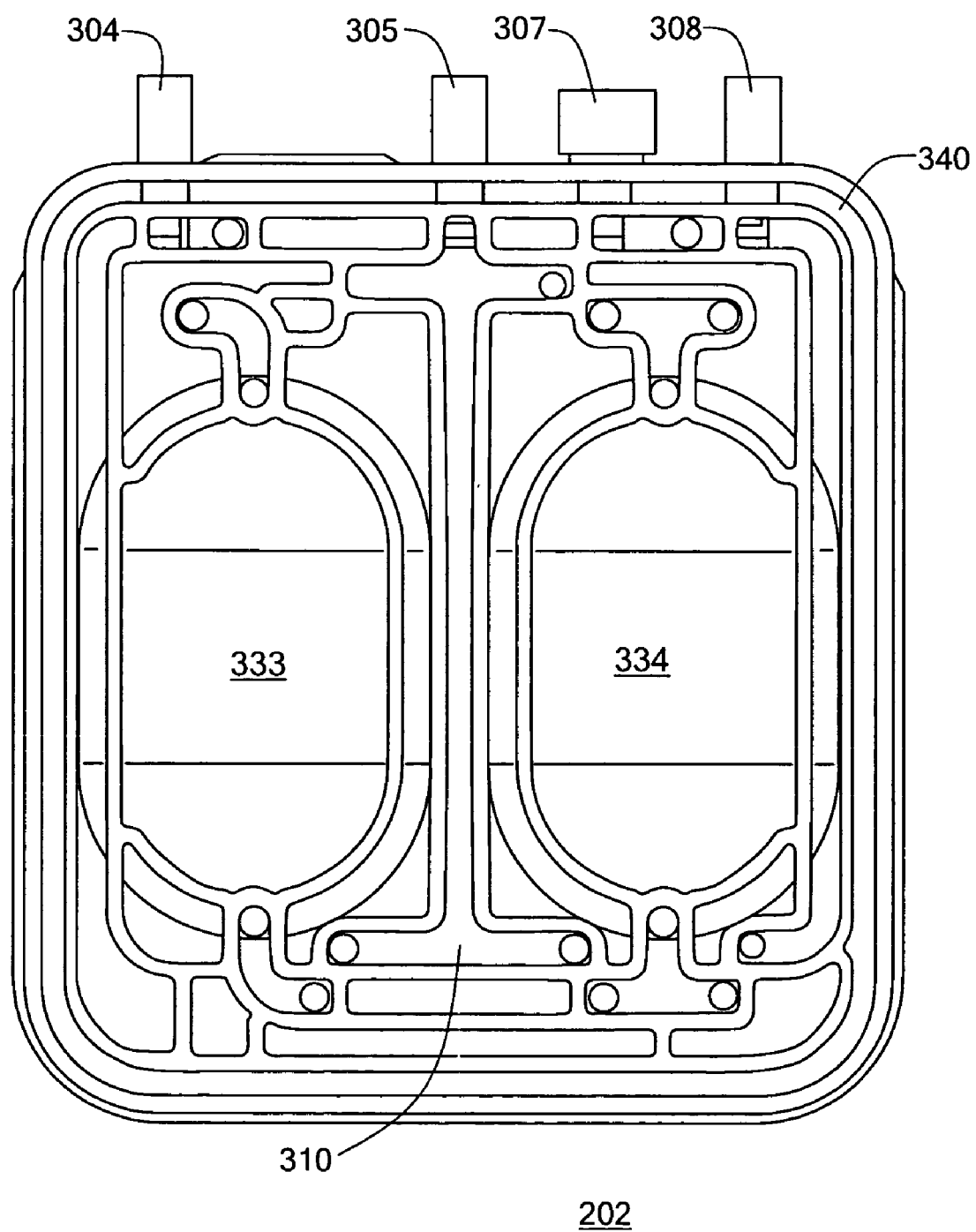
FIG. 3A shows a front view of the pump cassette.

FIG. 3A shows a front view of pump cassette 202. The pump cassette 202 is essentially a rigid core including formations and sealing ribs 340 constituting various pumping chambers, fluid valves, and fluid pathways (channels). The rigid core is covered on each side by a flexible membrane (e.g., a flexible PVC sheet). The flexible membranes seal against the core and isolate the blood pump 104 from fluids within the cassette. The pump cassette 202 is designed to interface with the blood pump 104 in only one direction. For example, the pump cassette 202 typically includes an asymmetric feature (such as the placement of tubing) that prevents the blood pump door from closing if the pump cassette 202 is inserted incorrectly.

Among other things, the pump cassette 202 includes a working solution inlet port 304, an RBC inlet port 305, a vent port 307, an outlet port 308 and two pumping chambers, namely a working solution chamber 333 and an RBC chamber 334. During blood processing, working solution from the working solution container 112 is drawn into the working solution chamber 333 through the tubing 210 and 212 and the working solution inlet port 304, and is pumped from the working solution chamber 333 into the channel 310 while RBCC from the RBCC container 106 is drawn into the RBC chamber 334 through the RBCC inlet tube 204, the RBCC inlet port 305, and the channel 310. This causes the working solution and RBCC to be mixed within the channel 310 and the RBC chamber 334. The mixture (incubation solution) is pumped from the RBC chamber 334 to the incubation bag 118 through the outlet port 308 and the incubation solution outlet tube 206.

Figure 3B:
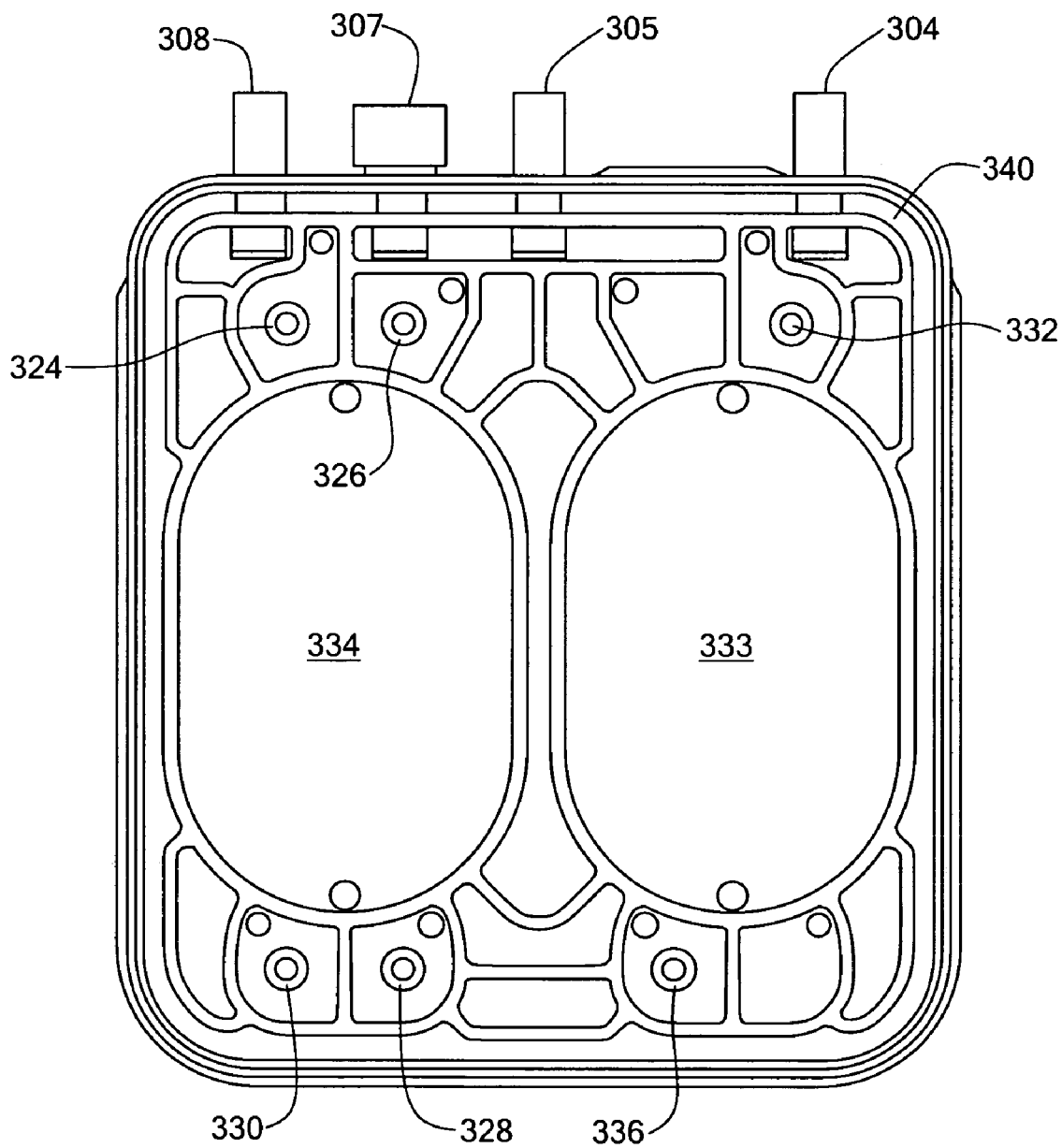
FIG. 3B shows a rear view of the pump cassette.

FIG. 3B shows a rear view of the pump cassette 202. The rears view of the pump cassette 202 shows various "volcano" valves that are used to open and close various fluid pathways within the pump cassette 202. The valves include an RBC priming valve 326, an RBC valve 328, an incubation bag valve 330, a working solution valve 332, and a working solution connection to RBC line valve 336. The volcano valves and the pumping chambers are all operated pneumatically from the rear of the pump cassette 202, as discussed below.

Blood Pump

As discussed above, each blood pump 104 prepares incubation solution by mixing an anti-pathogen solution with RBCC. A disposable pump cassette 202 is used to handle the various fluids. The pump cassette 202 serves as an interface between the blood pump 104, the RBCC container 106, and the incubation bag 118 so that no working solution, RBCC, or incubation solution comes into actual contact with the components of the blood pump 104. The blood pump 104 preferably uses pneumatics to operate the pump cassette 202 as well as other components, as discussed below.

The blood pump 104 produces the incubation solution by causing working solution to be drawn into the working solution chamber 333 and pumping working solution from the working solution chamber 333 into the channel 310 while drawing RBCC into the RBC chamber 334 through the channel 310. This causes the working solution and RBCC to be mixed within the channel 310 and the RBC chamber 334. The mixture (incubation solution) is pumped from the RBC chamber 334 to the incubation bag 118 through the outlet port 308.

Typically, the working solution is pumped from the working solution chamber 333 using a pulsing technique in which small quantities of working solution are pumped at predetermined intervals and the pulsing of working solution is adjusted periodically using a closed feedback loop in order to produce an incubation solution having a predetermined concentration of working solution, with predetermined limits. Specifically, the working solution is delivered in a pulsatile mode where the pulse width of the exit valve on the working solution chamber is controlled. The fluid valve is pulsed at a pulse width and interval that is predetermined for each pumping stroke and is adjusted stroke-by-stroke according to the amounts of working solution and RBCC pumped, as described below. The blood pump 104 can support pulse widths above some minimum value, and the interval between pulses is increased in order to achieve an effective pulse width below the minimum value.

The blood pump 104 preferably includes a library of generic pump control (N-Pump) functions. The N-Pump library functions are used to perform various generic pumping operations such as, for example, pumping fluid into a chamber of the pump cassette, pumping fluid out of a chamber of the pump cassette, measuring the amount of fluid pumped, performing air detection, and maintaining tank pressures. The blood pump 104 preferably also includes a Fluid Logic Module (FLM) that contains higher level functions that employ the N-Pump library functions to implement application-specific functions (such as specific logic for mixing the working solution with the RBCC to produce the incubation solution).

The blood pump 104 includes one master board connected to two pump boards that together perform the N-Pump and FLM functions. The master board communicates to each of the pump boards via a multi-drop RS 485 bus. Each pump board controls a single pump chamber of the pump cassette 202 and the valves on its board.

Figure 4:
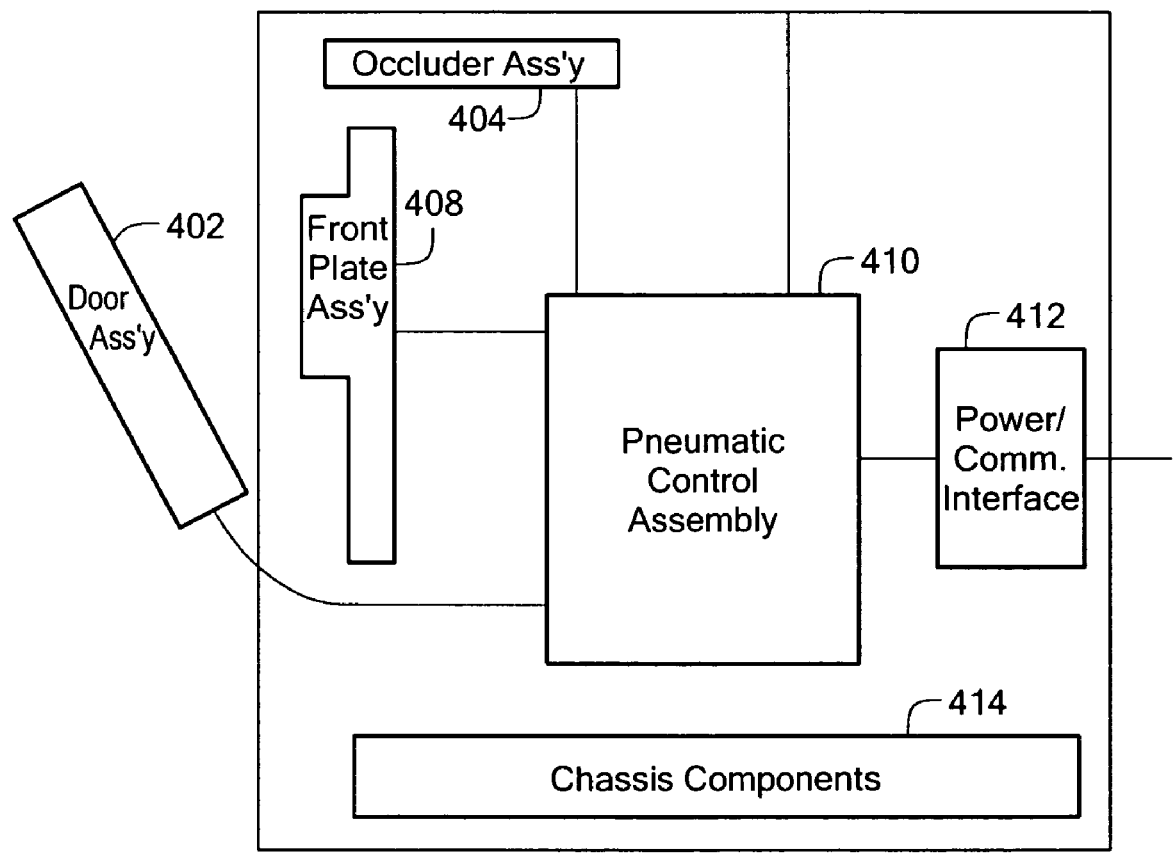
FIG. 4 shows a conceptual block diagram of the blood pump.

FIG. 4 shows a conceptual block diagram of an embodiment of the blood pump 104. Among other things, the blood pump 104 includes a door assembly 402, an occluder assembly 404, a front plate assembly 408, a pneumatic control assembly 410, a power/communication interface 412 including connectors for the 12-Volt power supply and the RS-232 communication link to the process controller 120, and chassis components 414. Each of these assemblies is discussed below.

Pneumatic Control Assembly

The pneumatic control assembly 410 provides positive and negative air pressure for operating the various other pneumatically controlled components and also acts as the general controller for the blood pump 104. The pneumatic control assembly 410 contains three electromechanical pump module assemblies, namely a tank management module assembly and two chamber module assemblies (one for the working solution pump chamber and one for the RBC pump chamber). Each pump module assembly includes an aluminum manifold, pneumatic valves, pneumatic fittings, a valve interface board, and an electronics board that includes pressure transducers and a dedicated microprocessor. The tank management module assembly handles all communication between the blood pump and the process controller 120, synchronizes pumping of the chamber module assemblies, maintains positive and negative air pressure in various accumulators, seals and unseals the door assembly, engages and disengages the occluders, monitors the door open/closed status, and monitors the air-in-line sensor, as described below. Each chamber management assembly controls a separate one of the pump chambers, and also controls the fluid valves associated with the pump chamber and measures the volume of liquids pumped through the pump chamber.

Figure 5A:
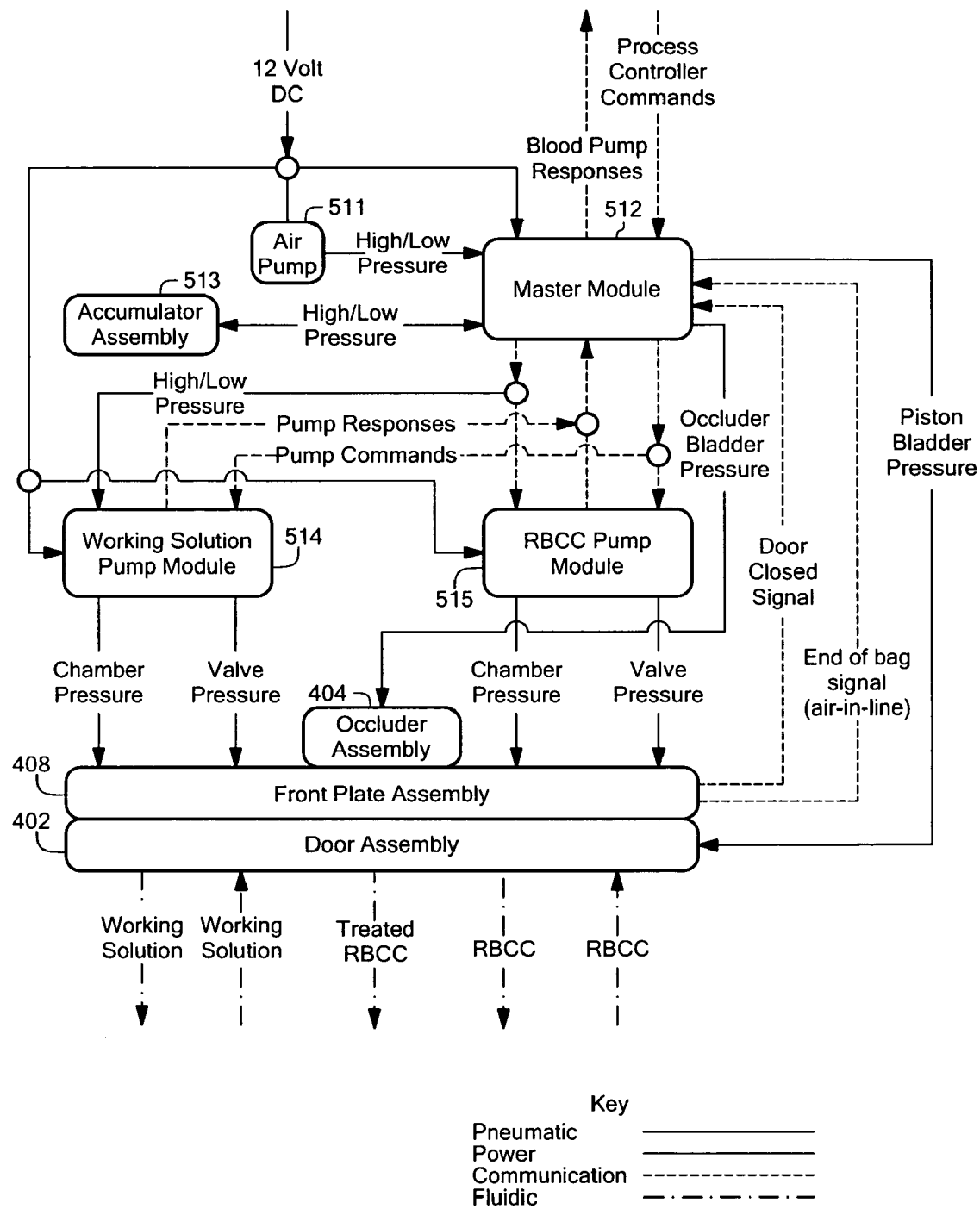
FIG. 5A is an architectural flow diagram showing the relationship between the pneumatic control assembly and the other assemblies.

FIG. 5A is an architectural flow diagram showing the relationship between the pneumatic control assembly 410 and other assemblies. In this figure, the pneumatic control assembly 410 is represented by master module 512, accumulator assembly 513, working solution pump module 514, and RBCC pump module 515. The air pump 511 is considered to be one of the chassis components 414. The air pump 511 generates high and low air pressure for the master module 512, which stores high and low air pressure in the accumulator assembly 513. The pneumatic control assembly 410 directs air pressure (positive and negative) to the various pneumatic mechanisms of the pump. The master module 512 pneumatically controls bladders in the occluder assembly 404 and a bladder in the door assembly 402, as discussed below. The master module 512 provides high and low air pressure to the working solution pump module 514 and the RBCC pump module 515. The working solution pump module 514 controls the working solution chamber 333 and associated valves of the pump cassette 202 through the front plate assembly 408, and the RBCC pump module 515 controls the RBC chamber 334 and associated valves of the pump cassette 202 through the front plate assembly 408, as described below.

Figure 5C:
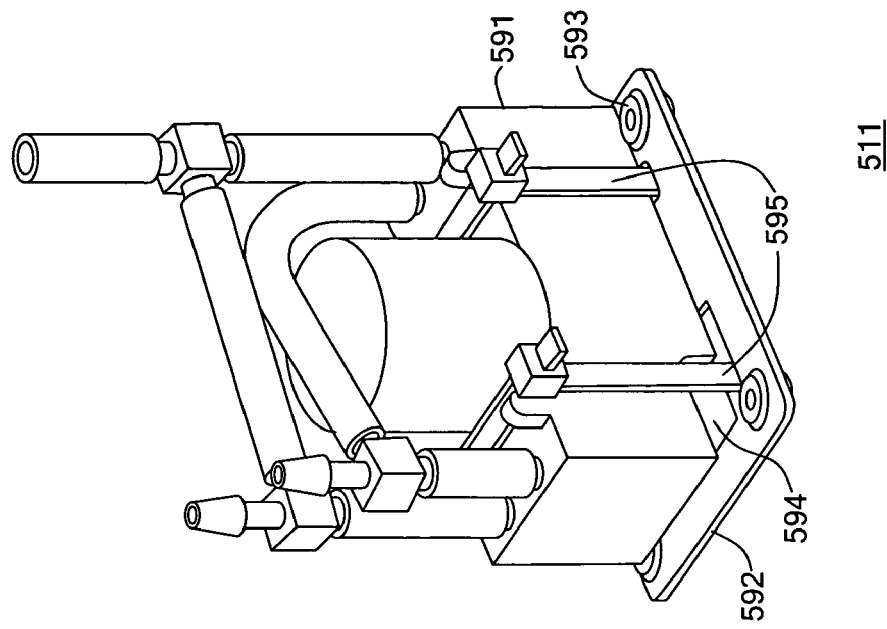
FIG. 5C shows an exemplary embodiment of the air pump.
Figure 5B:
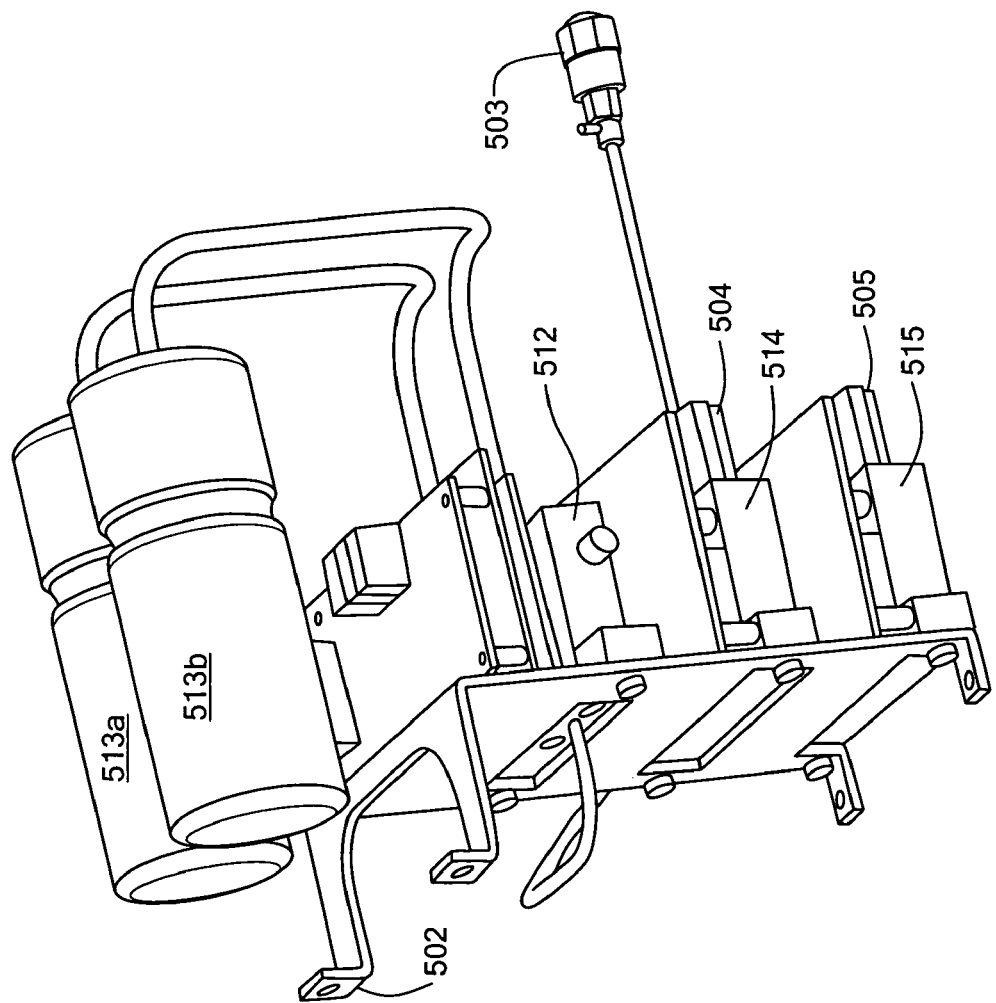
FIG. 5B shows an exemplary embodiment of the pneumatic control assembly.

FIG. 5B shows an exemplary embodiment of the pneumatic control assembly 410. Among other things, the pneumatic control assembly 410 includes manifold mounting bracket 502, a negative pressure accumulator (pressure bottle) 513a, a positive pressure accumulator (pressure bottle) 513b, a manual door vent mechanism 503, the Tank Management Module Assembly 512, the two Chamber Module Assemblies 514 and 515, and associated tubing and fittings.

The tank management module 512 includes an input/output (I/O) board, a CPU board, a valve-interface board, a pneumatic manifold system, pneumatic valves, pressure transducers 2-vent covers (mufflers), stand-offs, and associated tubing and fittings. The tank management module 512 is used to control the pressures in the accumulators 513, a bladder in the door assembly 402, and bladders in the occluder assembly 404. The I/O board contains electrical controls for controlling LEDs that provide status information to the operator. The pressure transducers are used to monitor the pressures of the accumulators 513 and the bladder in the door assembly 402.

In the un-powered state, the pneumatic valve that controls flow to the bladder in the door assembly 402 preferably shuts closed. This prevents the door from being opened in the event of a loss of power.

In the un-powered state, the pneumatic valves that control flow to the bladders in the occluder assembly 404 are preferably channeled to vent. This causes the occluders to occlude the tubing to prevent further flow of fluid through the tubing, as discussed below.

Each chamber module 514 and 515 includes a CPU board, a valve interface board, pneumatic manifold system, pneumatic valves (including a VSO (variable) valve), a VSX chamber (504 and 505 respectively), O-ring, copper mesh, vent cover (muffler), stand-offs, pressure transducers, and associated tubing and fittings. Each chamber module assembly controls the pneumatics for one of the pumping chambers and its associated valves. The VSX chambers 504 and 505 act as reference volumes in order to measure the volume of fluid that is delivered with the FMS system. The pressure transducers are used to monitor the pressure of the VSX chamber, and of the pumping chamber. The positive pneumatic system contains a pressure relief valve to prevent the air pump from pressurizing the positive system to greater than 16.0 psig.

In the un-powered state, all of the pneumatic valves preferably open the fluid valves to the positive pressure line. This ensures that the fluid valves are closed if there is a loss of power.

The blood pump 104 typically includes three microprocessor systems, one on the tank management module 512 and one on each of the chamber modules 514 and 515. These three microprocessor systems monitor each other for normal operation. Each microprocessor system also monitors key internal processes and data for validity. If any of these monitors fail, a failsafe line permits any of the three processors to stop pumping operations, close all of the fluid valves and occluder, and send an anomaly signal to the process controller. If the blood pump 104 detects an anomaly with the commands received from the process controller (e.g., commands received out of sequence), then the blood pump 104 will stop fluid flow and send an anomaly signal to the process controller.

FIG. 5C shows an exemplary embodiment of the air pump 511 in accordance with an embodiment of the present invention. The air pump 511 includes a pump motor 591 mounted to a pump plate 592 using double-sided tape 594 and two miniature nylon cable ties 595. Four ribbed isolator grommets 593 are inserted into corresponding openings in the pump plate 592.

Front Plate Assembly

The front plate assembly 408 includes all necessary pneumatic pathways to interface to the disposable pump cassette 202. The front plate assembly 408 includes, in accordance with the present invention, a bezel and a bezel gasket through which the pump cassette 202 is operated. During operation of the blood pump 104, the pump cassette 202 is positioned in the door assembly 402 and is pressed against the front plate assembly 408 in alignment with the bezel and bezel gasket by a bladder in the door assembly 402, as discussed below. Air lines connected to the bezel from the pneumatic control assembly 410 are used to displace membranes of the bezel gasket to operate the various valves and chambers of the pump cassette 202.

Figure 6A:
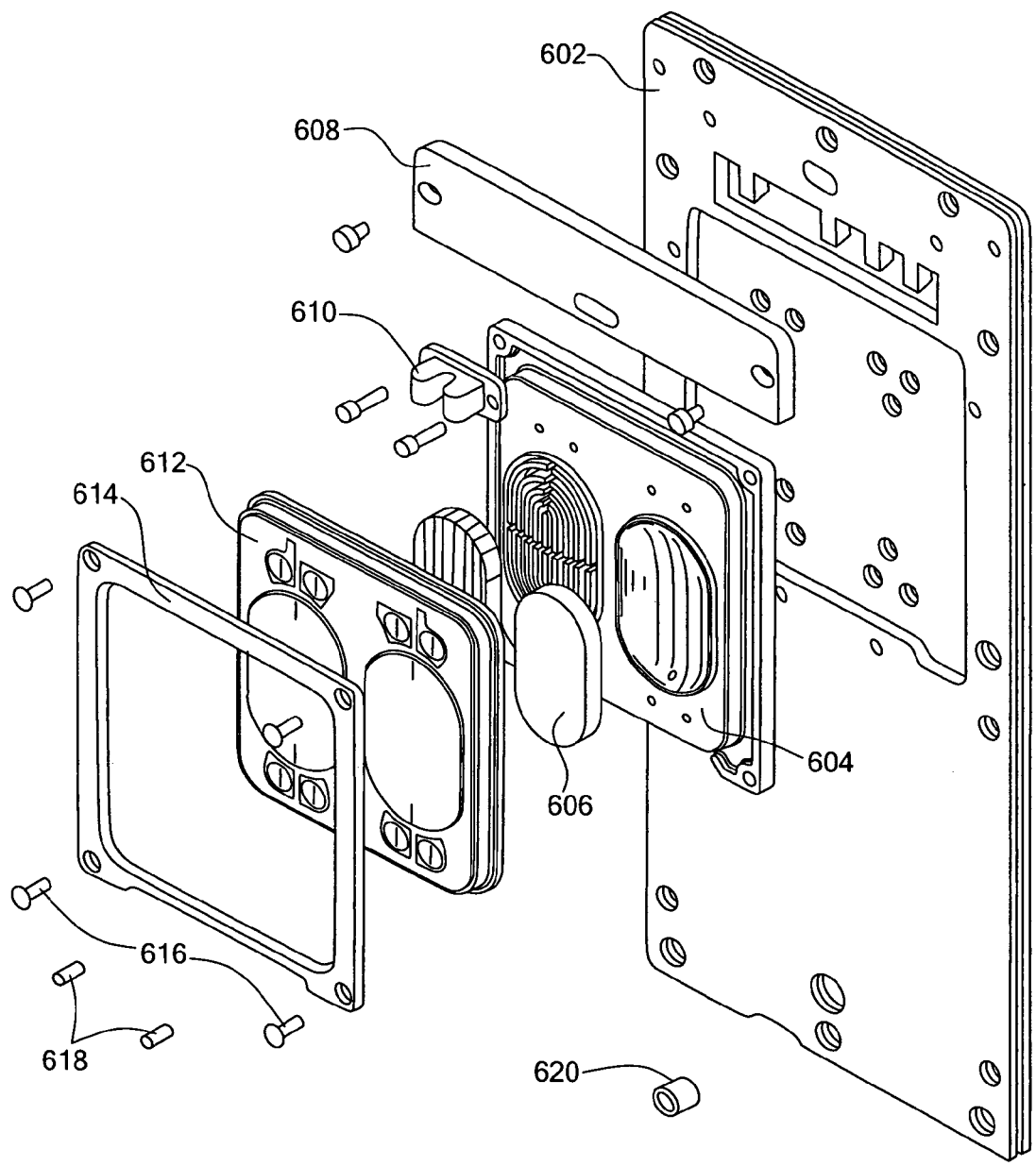
FIG. 6A shows an exploded view of an exemplary front plate assembly in accordance with an embodiment of the present invention.

FIG. 6A shows an exploded view of an exemplary front plate assembly 408 in accordance with an embodiment of the present invention. Among other things, the front plate assembly 408 includes a rigid front plate 602 to which are mounted a bezel 604, chamber foam 606, spacer 608, air-in-line sensor 610, bezel gasket 612, gasket retainer 614, hardware 616, dowel pins 618, and grommet 620. The bezel 604, chamber foam 606, and bezel gasket 612 are mounted to the front plate 602 by the gasket retainer 614 and associated hardware 616, forming a bezel assembly. This bezel assembly is used to control pumping and mixing of fluids using the pump cassette 202, as described below. The front plate 602 includes holes for allowing air tubes to pass between the rear of the bezel 604 and the pneumatic control assembly 410, which is typically situated behind the front plate 602. The front plate 602 also includes openings for occluder blades and for engaging a door latch mechanism, as described below. The air-in-line sensor 610 is positioned so as to align with and engage the RBCC inlet tube 204, and is used during blood processing to detect air in the RBCC inlet tube 204 indicating that there is no more RBCC to be processed.

Figure 6B:
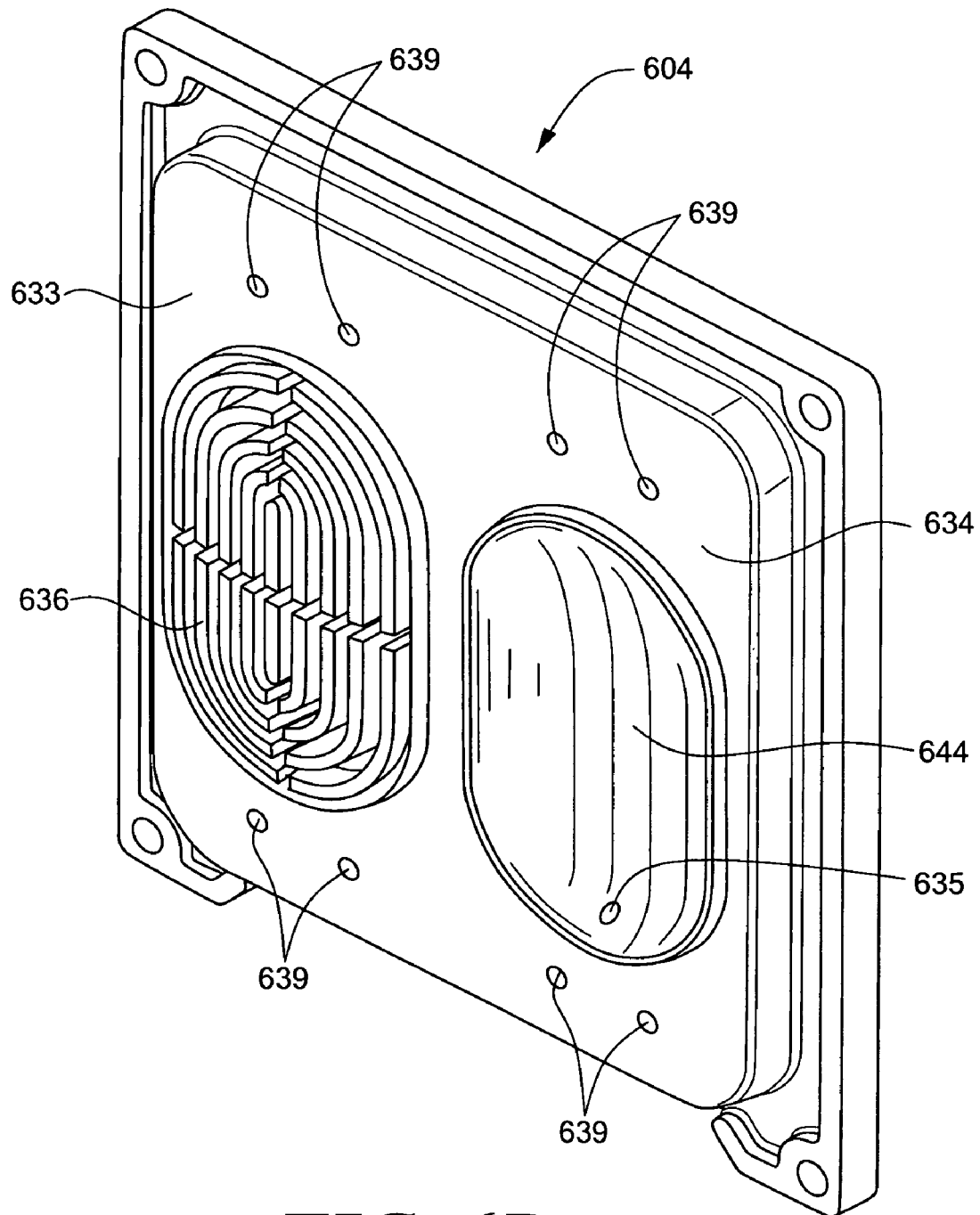
FIG. 6B shows a perspective front view of an exemplary bezel in accordance with an embodiment of the present invention.

FIG. 6B shows a view of the pumping side of an exemplary bezel 604 in accordance with an embodiment of the present invention. The bezel 604 is a rigid block. The block is preferably made as a molded polycarbonate/ABS unit. The bezel 604 includes a depression 622 having a chamber wall 624 up from which extend rib structures 636 that form an elevated contour above the pumping side of the rigid block. The bezel 604 is typically molded with the rib structures 636, for example, using a mold with integral rib formations or a "blank" mold (i.e., without integral rib formations) and a mold insert having rib formations. The depression 622 has at least one and preferably two cavities 635 therein. The cavities 635 are in fluid communication with ports that connect to air lines out the back of the bezel. The rib structures 636 allow pneumatic pressure to be applied over the elevated contour.

The elevated contour of the ribs 636 limits the pump stroke volume making the ribbed depression suitable for actuating the working solution chamber 333 of the pump cassette 202. The bezel gasket 612 fits over the pumping side of the rigid block sealing the air paths. As positive pressure is applied through one or more cavities into the depression beneath the ribs the gasket membrane 613 covering the ribs is forced away from the pumping side to push against the working solution chamber. When negative pressure is applied through the one or more cavities, the gasket membrane 613 is pulled against the elevated contour of the ribs pulling a small amount of working solution into the working solution chamber.

Referring with greater particularity to the rib structures 636 of the preferred embodiment, it is noted that the rib structures 636 are arranged so as to provide a symmetrical grid of air passages as shown in FIG. 6C. Moreover, the elevated contour may be in the shape of a mound that increases in height from a perimeter of the depression to a middle of the mound as seen in FIGS. 6D and 6E. The depression has two cavities 635 therein and the ribs 636 provide a plurality of air passages 642 between the two cavities. In the particular arrangement, the ribs 636 leave a straight air passage 640 unobstructed at each of the two cavities, such that at each of the two cavities the respective straight air passage 640 connects the cavity to the plurality of air passages 642 between the two cavities. The ribs 636 and the air passages 642 formed thereby run parallel to the perimeter of the depression. In this case, the depression is oval shaped and the ribs are aligned with the perimeter. It is desirable for the arrangement of ribs to distribute the air pressure in a relatively even manner across the elevated contour to provide an evenly distributed pull and push against the working solution chamber.

The bezel 604 includes a second depression 644 with two cavities 635 for operating the RBC chamber 334 of the pump cassette 202. This depression 644 lacks ribs allowing for a larger volume to be pulled and pushed through the RBC chamber in each stroke as compared to the working solution chamber. The bezel 604 further includes various valve cavities 639 for operating the various valves of the pump cassette 202.

Figure 6G:
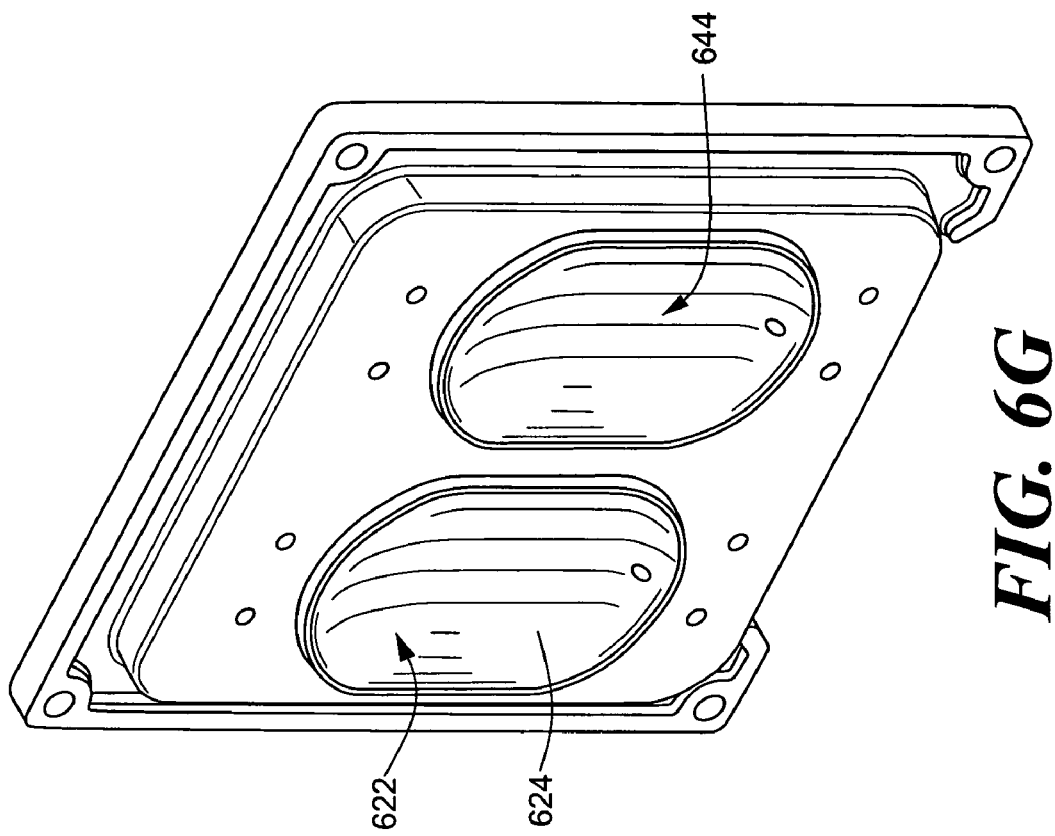
FIG. 6G shows a perspective front view of the bezel of FIG. 6B with the ribs machined away.
Figure 6F:
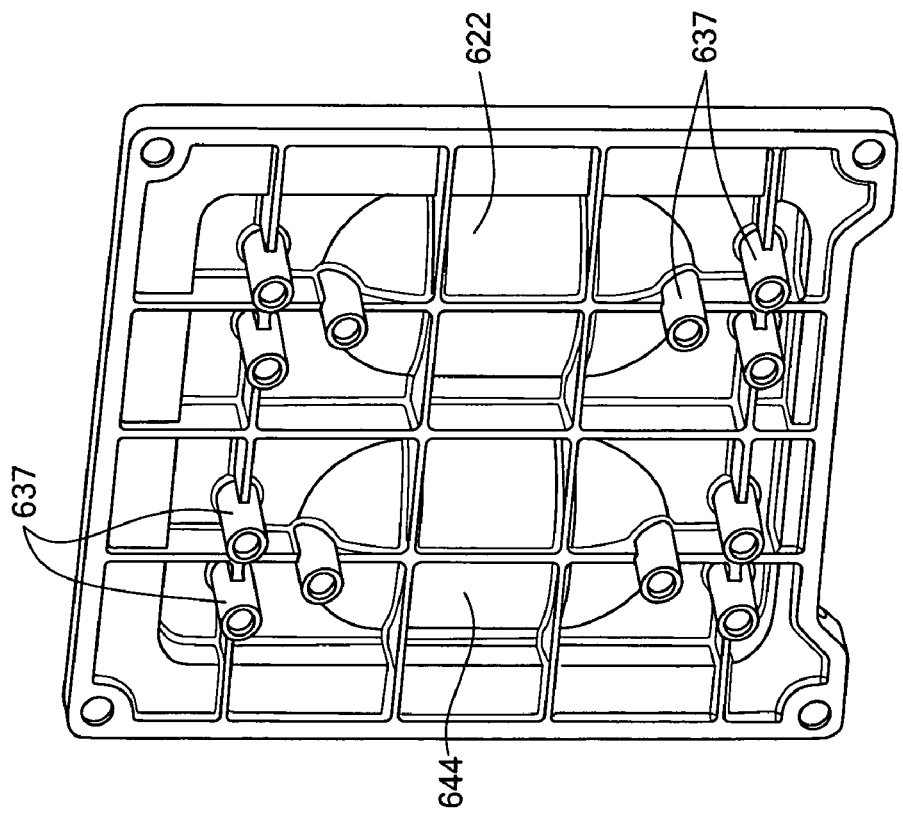
FIG. 6F shows a perspective rear view of the bezel of FIG. 6B.

FIG. 6F shows a view of the back side of the bezel 604 in accordance with an embodiment of the present invention. The bezel 604 includes ports 637 to which pneumatic tubing from the pneumatic control assembly 410 are connected. The ports are hollow tubular structures, in particular, solvent bondable tubing connections integrally molded with the rigid block. In this embodiment, each of the cavities 635, 639 is in fluid communication with a single port 637. The port may have an inner diameter larger in size than the cavity in fluid communication therewith. The integral ports 637 allow the pneumatic connections to be made without an added expense from threaded fittings or O-rings.

Unlike the blood pump 104, the compounder 102 requires a bezel with two full volume depressions. In accordance with an embodiment of the present invention, the bezel 604 is designed so that the single molded rigid block can also be used as the compounder bezel as shown in FIG. 6G. The depression 622 beneath the rib structures 636 has a chamber wall 624. Removal of the ribs leaves an open chamber defined by the chamber wall 624. The ribs may be removed from the molded bezel by precision machining, such as milling.

Although the ribs are preferably molded or otherwise integral to the bezel and are removable if needed, a ribbed bezel assembly can alternatively be formed by coupling a rib insert into a depression of the bezel. The rib insert would typically be configured substantially as shown and described above, but would be a separate component. The rib insert could be coupled into a depression of the bezel in any of a variety of ways. For example, the rib insert could be snapped into the depression, for example using tabs on the rib insert that are engaged by corresponding slots on the bezel, or the rib insert could be glued or otherwise attached to the bezel.

Figure 6I:
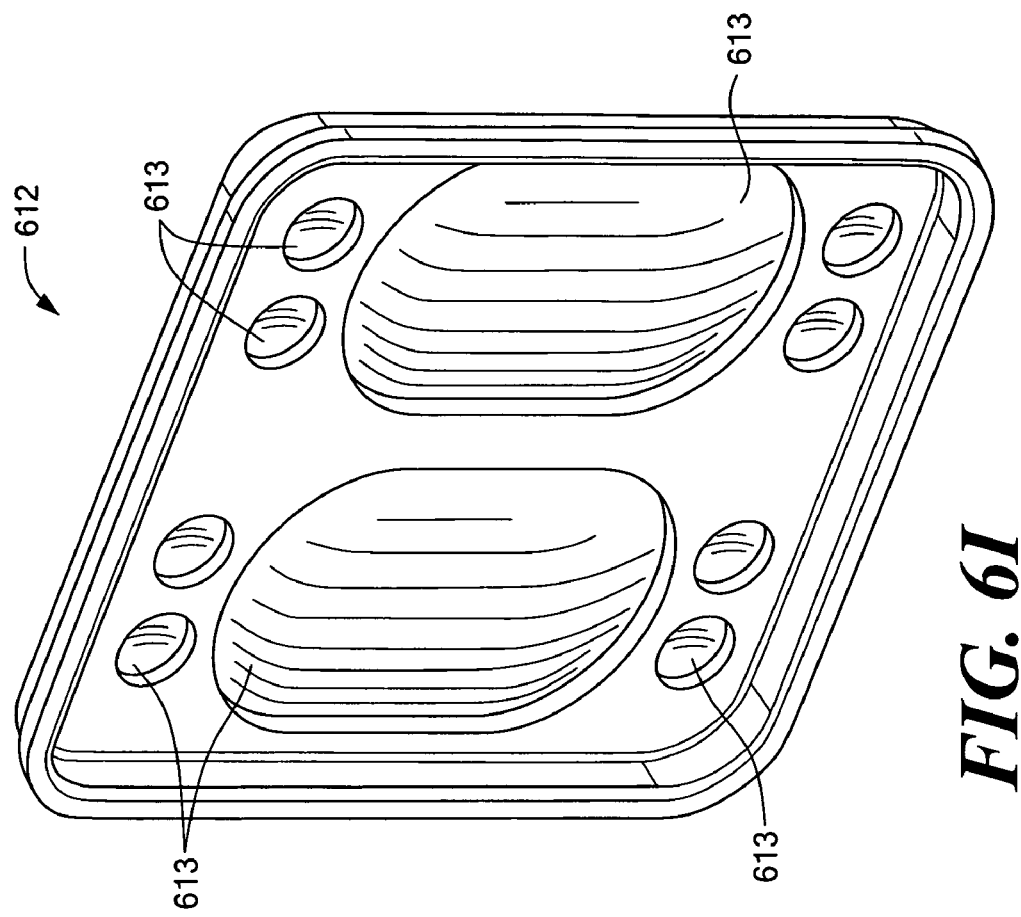
FIG. 6I shows a perspective rear view of the bezel gasket of FIG. 6H.
Figure 6H:
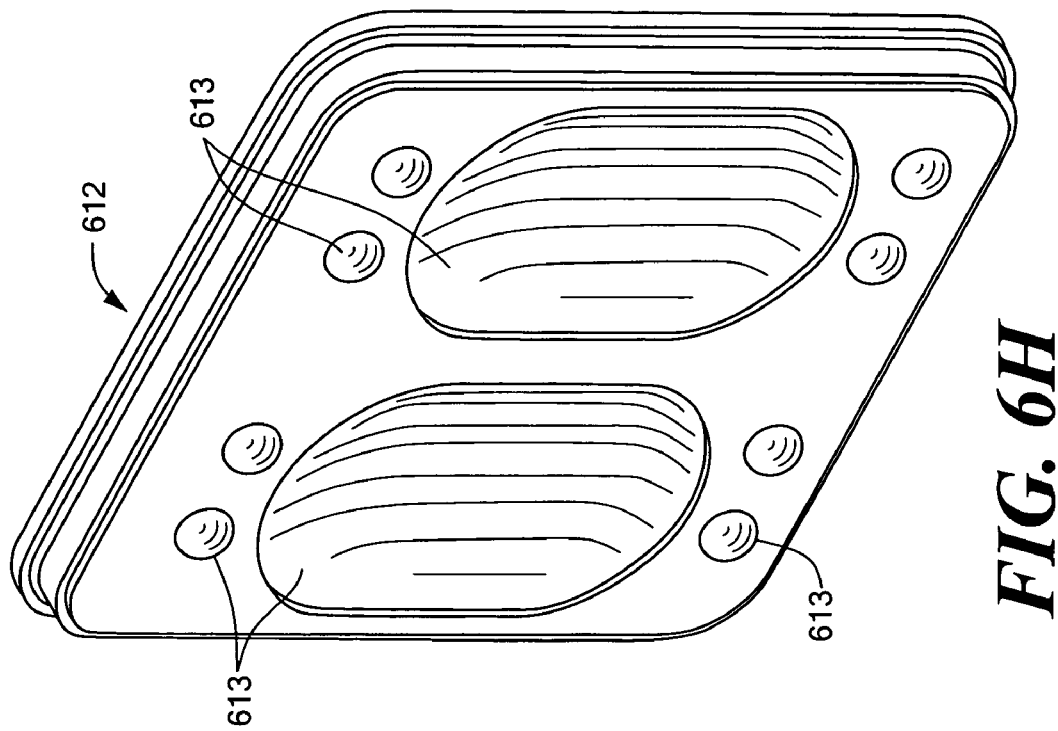
FIG. 6H shows a perspective front view of a bezel gasket for use with the bezel of FIG. 6B.
Figure 6J:
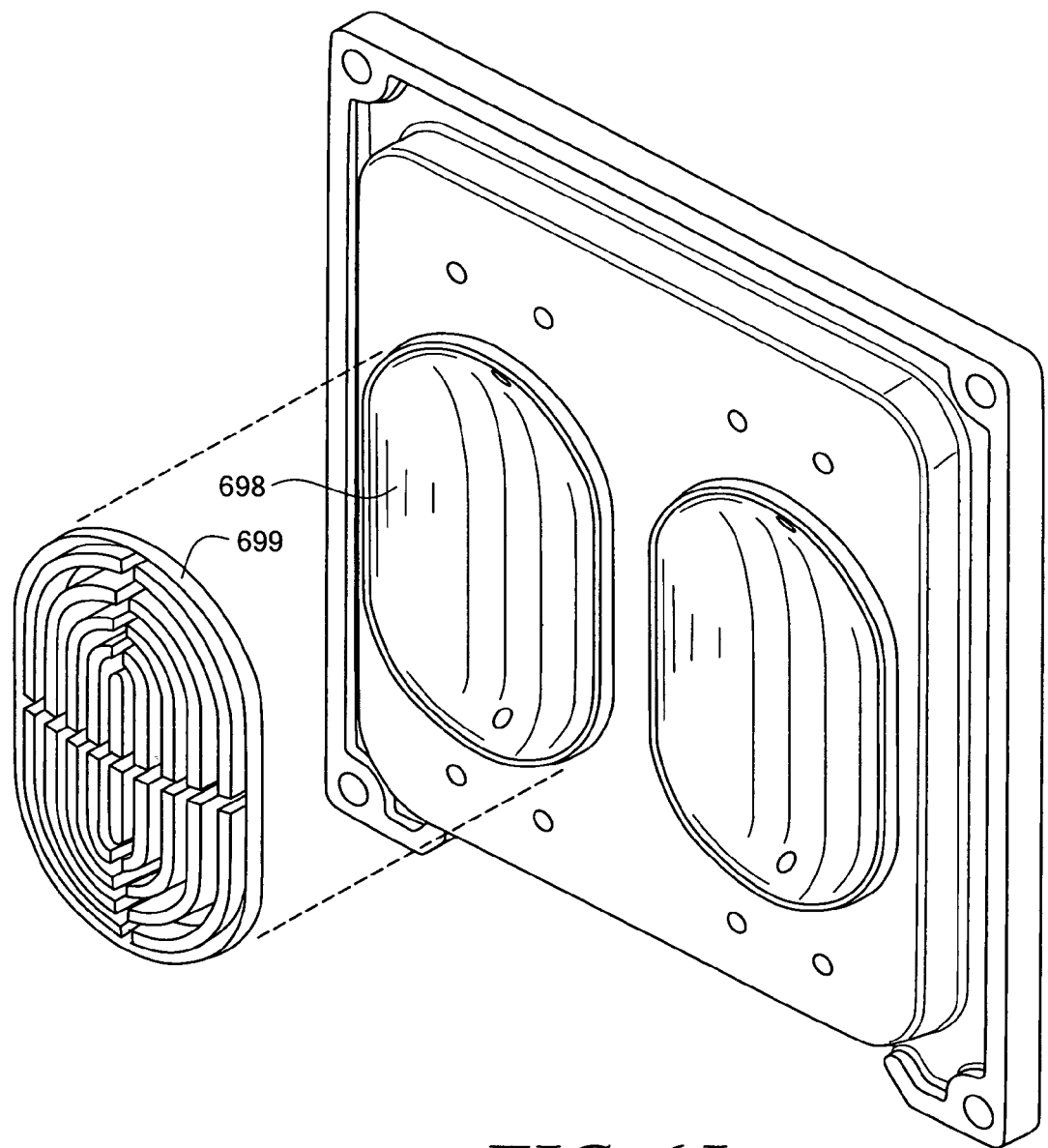
FIG. 6J shows an exploded view of a bezel assembly including a rib insert for adding ribs to a bezel in accordance with an embodiment of the present invention.

FIG. 6J shows an exploded view of a bezel assembly including a rib insert in accordance with an embodiment of the present invention. The bezel includes an open depression 698. The rib insert 698 is coupled to the bezel so as to fit within the depression 698. The rib insert 699 is typically shaped to match the contour of the depression, and the ribs typically extend above the surface of the bezel.

FIG. 6H shows a front view of an exemplary bezel gasket 612 in accordance with an embodiment of the present invention. The bezel gasket 612 fits over the front of the bezel 604 and acts as an interface between the bezel 604 and the pump cassette 202 for sealing the fluid paths of the bezel 604 and for actuating the chambers and valves of the pump cassette 202. The pump cassette 202 is pressed firmly against the front side of the bezel gasket 612 during blood processing in order to produce an air-tight seal between the bezel gasket 612 and the pump cassette 202. The bezel gasket 612 includes membranes 613 that correspond to the depressions and the valve cavities. If desired, chamber foam 606 may be inserted between the chamber membrane and the ribs or depressions in the bezel. The chamber foam 606 allows air to pass through it and serves to fill some space between the bezel and the membrane. Positive and negative air pressure produced through the bezel cavities operate on the bezel gasket membranes 613, which in turn operate on the chambers and valves of the pump cassette 202.

FIG. 6I shows a rear view of an exemplary bezel gasket 612 in accordance with an embodiment of the present invention. The rear side of the bezel gasket 612 contacts the pumping side of the bezel 604, and is pressed firmly against the bezel 604 during blood processing in order to produce an air-tight seal.

Door Assembly

The door assembly 402 mounts to the front plate assembly 408, and provides a means to load and align the disposable pump cassette 202 within the blood pump 104. The door assembly 402 provides a force on the pump cassette 202 against the bezel assembly of the front plate assembly 408 in order to provide sealing of the cassette's fluid paths and valves, as described in greater detail in Application D73. The door assembly 402 includes a special latch system that helps maintain the seal, and also helps prevent accidental opening of the door during blood processing, as described in greater detail in Application D74. The door assembly 402 also provides a surface for the occluders to function against, as described below.

Figure 7A:
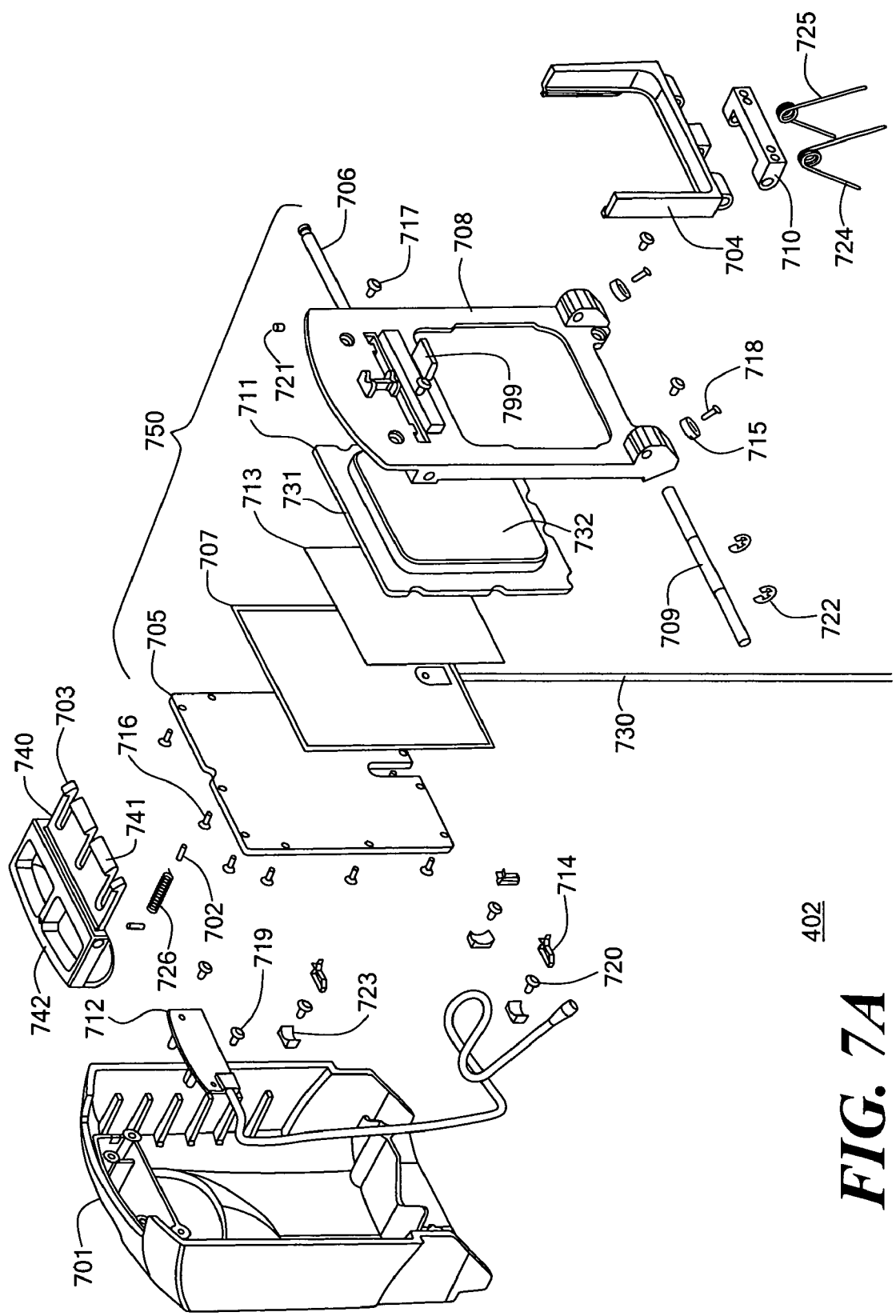
FIG. 7A shows an exploded view of the door assembly.

FIG. 7A shows an exploded view of the door assembly 402 in accordance with an embodiment of the present invention. Among other things, the door assembly 402 includes a door cowl 701, a latch spring post 702, a door latch 703, a cassette receptacle 704, a back plate 705, a latch pin 706, a pneumatic interface plate 707 with an attached pneumatic circuit 730, a frame 708, a door pin 709, a door mounting bracket 710, a piston assembly 711 including a piston 732 attached to an inflatable bladder within a piston plate 731, a human interface board assembly 712, double coated tape 713, a miniature cable tie 714, recessed bumpers 715, E-rings 722, cable tie mount 723, torsion springs 724 and 725, extension spring 726, a cassette orientation tab 799, and various screws 716, 717, 718, 719, 720, and 721. The human interface board assembly 712 is mounted to the inside of the door cowl 701. The pneumatic interface plate 707, double coated tape 713, and piston assembly 711 are sandwiched between the back plate 705 and the frame 708, which are mechanically coupled together to form a frame assembly 750. The door latch 703 is positioned so that a handle portion is accessible from a front side of the door cowl 701. The frame assembly 750 is mounted to the inside of the door cowl 701 so that a latch portion of the door latch 703 protrudes through the frame assembly 750 and the frame assembly 750 holds the door latch 703 in place. The cassette receptacle 704 is pivotally mounted to the frame 708 using the door mounting bracket 710, the door pin 709, and the E-rings 722. Recessed bumpers 715 reduce strain on the door if the door is opened too far or with excessive force. The torsion springs 724 and 725 aid the operator in closing the door, as the door has considerable weight due to the many components. The cassette orientation tab 799 prevents the door from being closed if the pump cassette is oriented incorrectly in the cassette receptacle 704.

The door assembly is designed to permit single-handed operation, specifically by pulling up on the handle. However, the door latch 703 is designed so that the door cannot be easily opened when the pump cassette is in place in the cassette receptacle 704 with the door closed and the bladder of the piston assembly 711 is inflated. Specifically, the latch portions of the door latch 703 have undercuts that are engaged by recesses in the front plate assembly 408. When the pump cassette is in place in the cassette receptacle 704 with the door closed and the piston assembly 711 is inflated so as to push the pump cassette against the bezel components of the front plate assembly 408, a sufficient force is generated between the door assembly 402 and the front plate assembly 408 to prevent the door handle from being easily lifted.

This door locking mechanism is described in greater detail in Application D74.

Figure 7B:
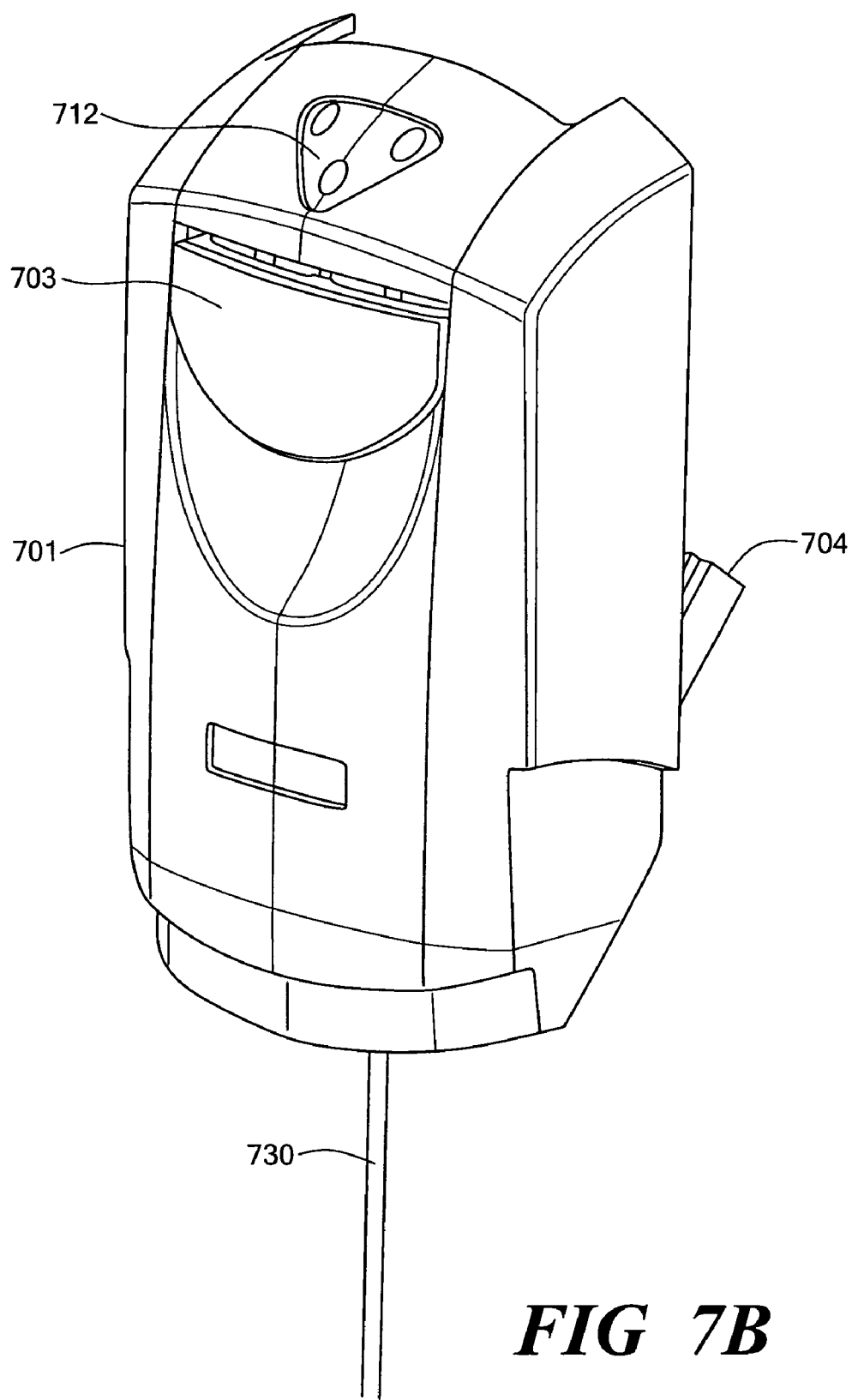
FIG. 7B shows a front perspective view of the door assembly.

FIG. 7B shows a front perspective view of the door assembly 402 in accordance with an embodiment of the present invention. The human interface board assembly 712 having LEDs and the handle portion of the door latch 703 are visible from the front of the door cowl 701. A portion of the cassette receptacle 704 and a portion of the pneumatic circuit 730 are also visible.

Figure 7C:
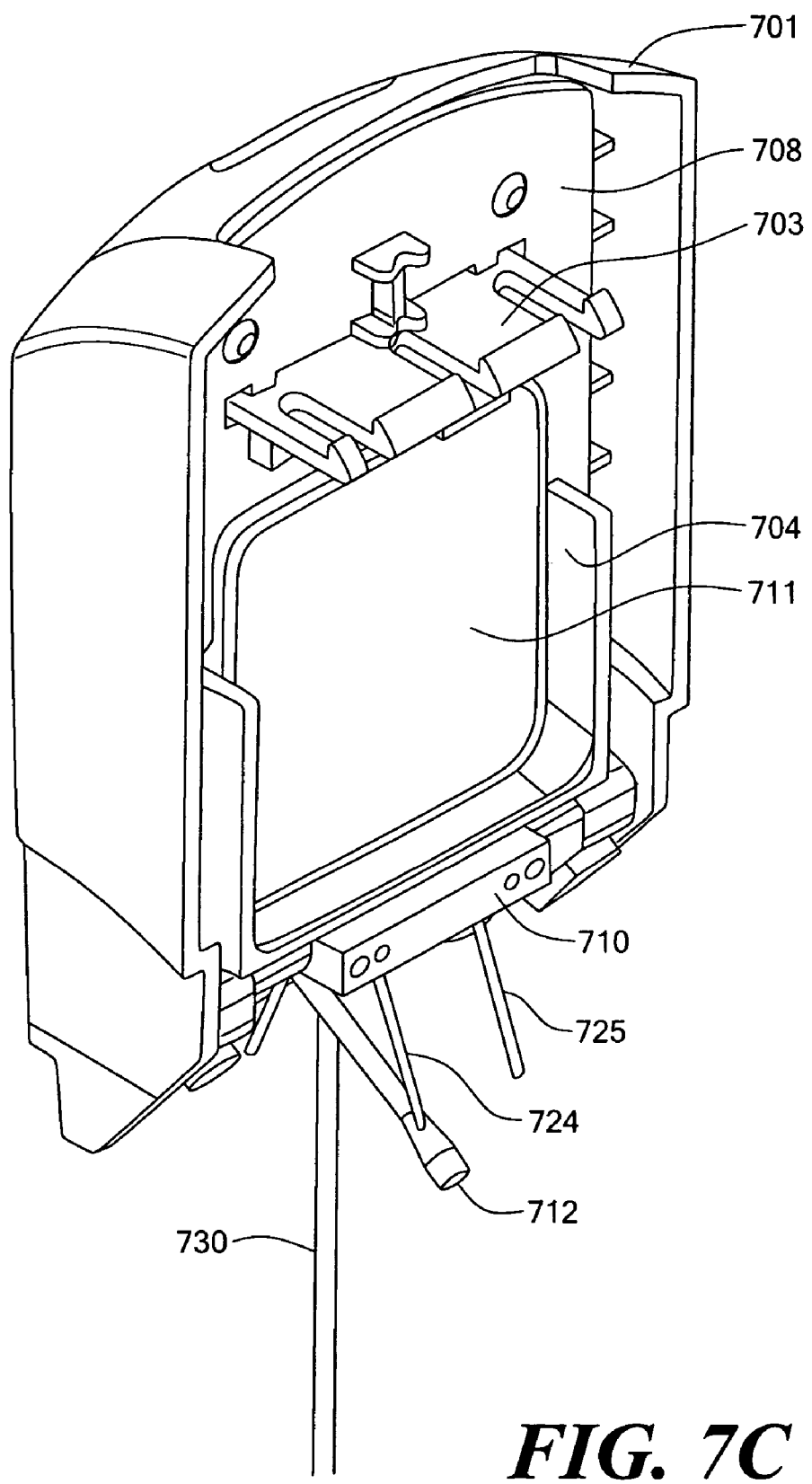
FIG. 7C shows a rear perspective view of the door assembly, in which the cassette receptacle is in a retracted position.

FIG. 7C shows a rear perspective view of the door assembly 402 in accordance with an embodiment of the present invention, in which the cassette receptacle 704 is in a retracted position. Visible at the rear of the door cowl 701 are the frame 708, the latch portion of the door latch 703, the cassette receptacle 704, the piston assembly 711, the door mounting bracket 710, the torsion springs 724 and 725, a portion of the human interface board assembly 712, and a portion of the pneumatic circuit 730.

Figure 7D:
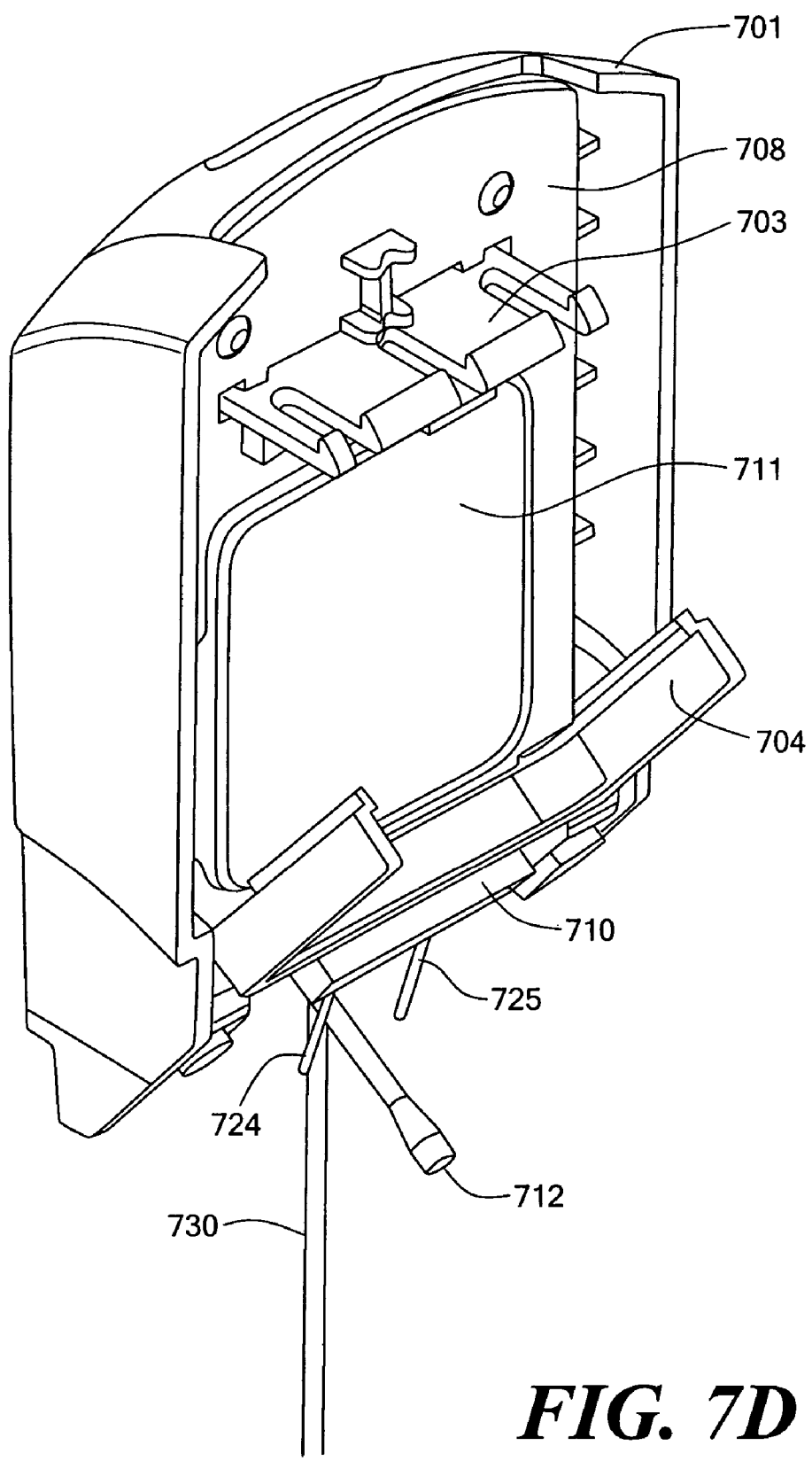
FIG. 7D shows a rear perspective view of the door assembly, in which the cassette receptacle is in an open position.

FIG. 7D shows a rear perspective view of the door assembly 402 in accordance with an embodiment of the present invention, in which the cassette receptacle 704 is in an open position. Visible at the rear of the door cowl 701 are the frame 708, the latch portion of the door latch 703, the cassette receptacle 704, the piston assembly 711, the door mounting bracket 710, the torsion springs 724 and 725, a portion of the human interface board assembly 712, and a portion of the pneumatic circuit 730.

Occluder Assembly

The occluder assembly 404 mounts to the back of the front plate assembly 408, and is used to selectively occlude the RBCC inlet tube 204, the incubation solution outlet tube 206, and the working solution distribution tube 212 as needed for testing, blood processing, and protection in the event of a failure. In the blood pump 104, the occluder assembly 404 includes two occluders, one operating on both the RBCC inlet tube 204 and the incubation solution outlet tube 206, and the other operating on the working solution distribution tube 212. The occluders are controlled pneumatically, and can be controlled independently.

In a typical embodiment, each occluder includes an occluder blade that is operated by a flat spring and an inflatable bladder. The occluder blade is coupled to one end of the spring. When the bladder is deflated, the spring extends the occluder blade into an occluding position, which blocks the passage of fluid through the tube(s). When the bladder is inflated, the bladder bends the spring so as to retract the occluder blade from the occluding position, which enables the passage of fluid through the tube(s). In the event of a loss of pneumatics, the occluder defaults to the occluded position so as to prevent fluid from passing through the tubing.

Figure 8:
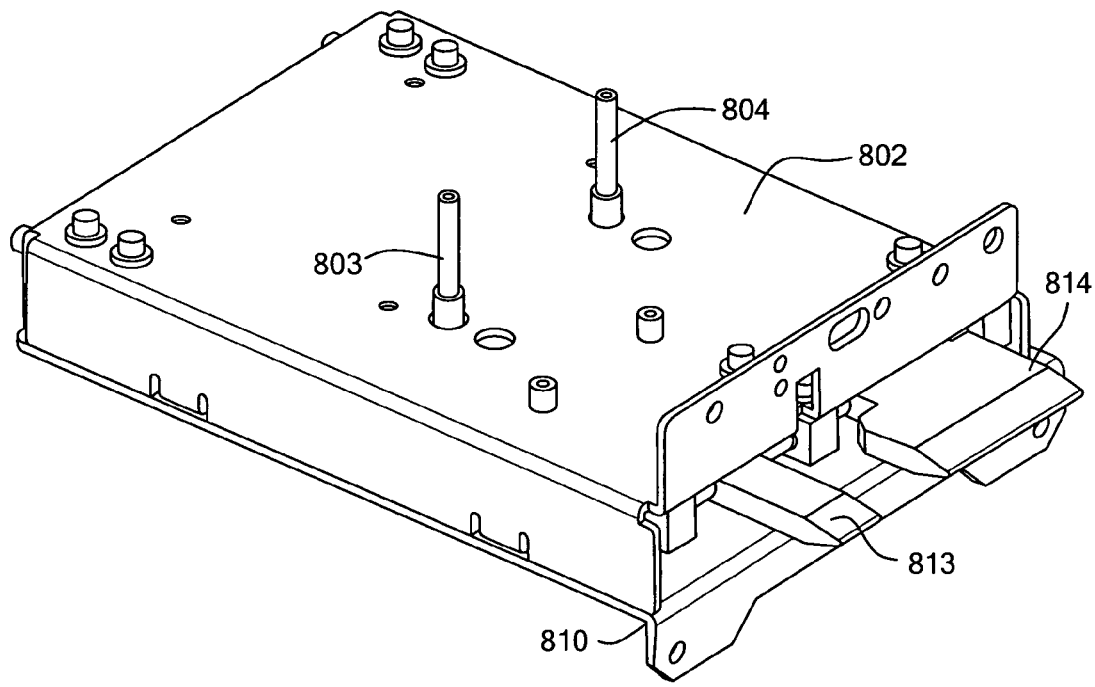
FIG. 8 shows a side perspective view of the occluder assembly.

FIG. 8 shows a side perspective view of the occluder assembly 404. The occluder assembly 404 includes, among other things, a bottom housing 801, a top housing 802, a first occluder having an occluder blade 813 and other components operated pneumatically through tube 803, and a second occluder having an occluder blade 814 and other components operated pneumatically through tube 804. The occluder assembly 404 is mounted to the front plate assembly 408, with the occluder blades 813 and 814 protruding through slots in the front plate assembly 804. The tubes 803 and 804 are connected to the pneumatic control assembly 410.

Figure 9:
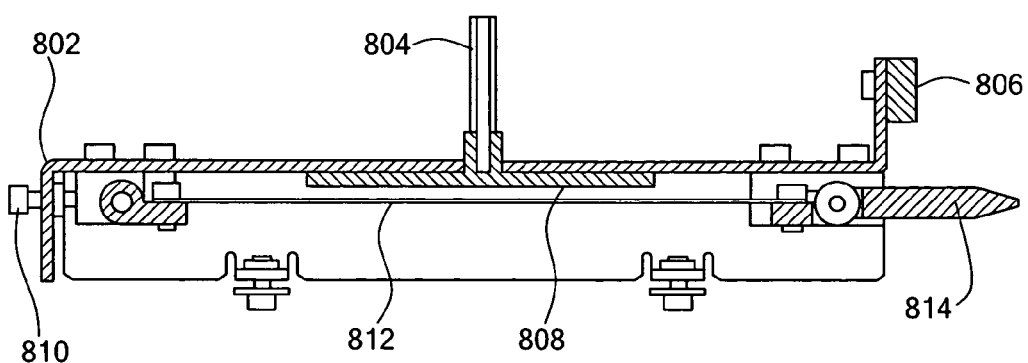
FIG. 9 shows a cross-sectional view of an occluder.

FIG. 9 shows a cross-sectional view of an occluder. Among other things, the occluder includes a flat occluder spring 812 having a rear end coupled to the top housing 802 and a front end coupled to the occluder blade 814, a bladder 808 situated between the top housing 802 and the spring 812, the tube 804 coupled to the bladder 808, and an adjuster 810 for adjusting the protrusion of the occluder blade 814. When the bladder 808 is inflated, the occluder spring 812 is deflected downward at the middle so as to shorten the effective length of the occluder spring 812 and retract the occluder blade 814. When the bladder 808 is deflated, the occluder spring 812 extends flat and therefore extends the occluder blade 814. The occluder blade 814 moves within guides (not shown) that allow the spring to extend and retract the occluder blade 814.

Figure 10:
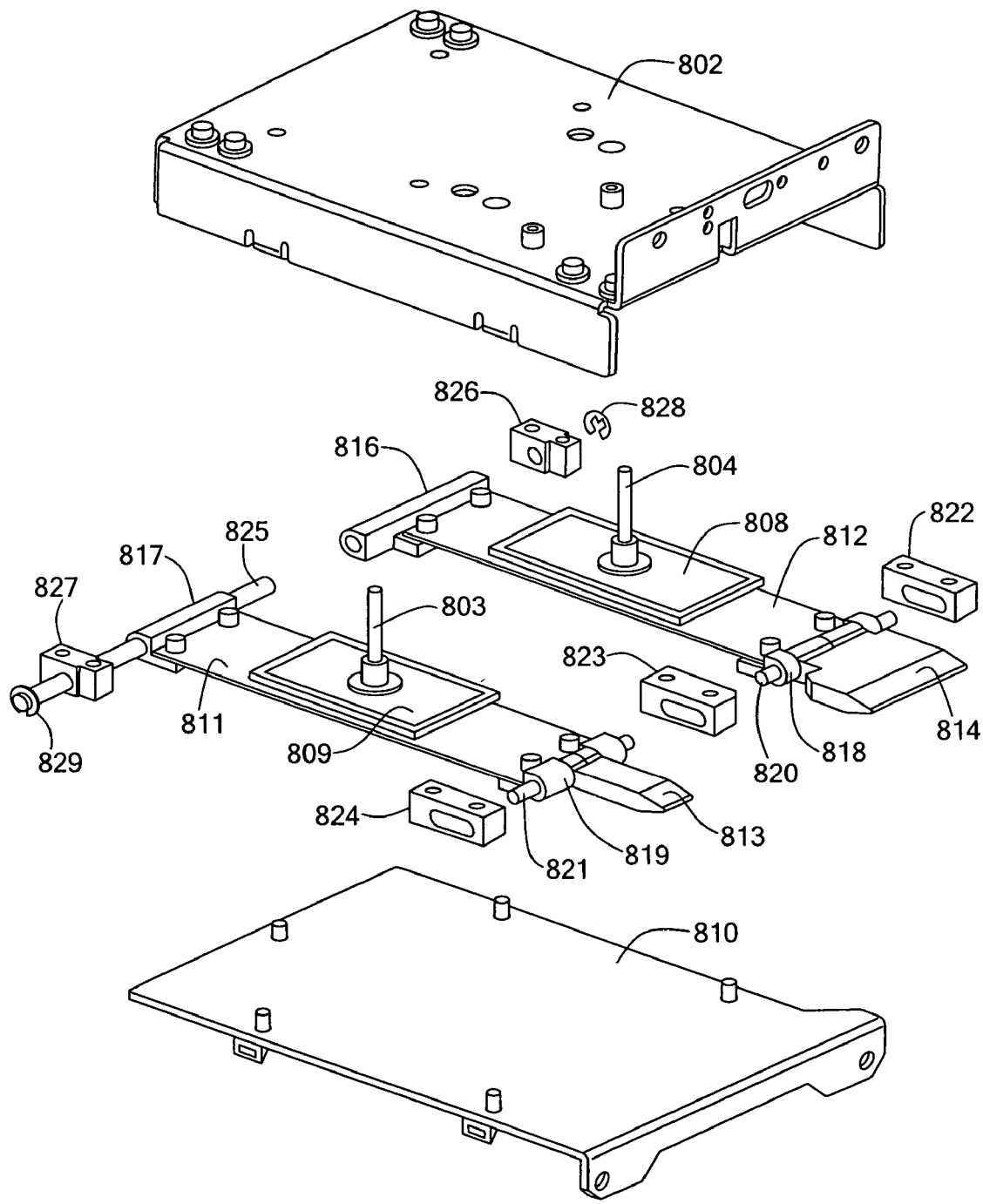
FIG. 10 shows an exploded view of the occluder assembly.

FIG. 10 shows an exploded view of the occluder assembly 404 in accordance with an embodiment of the present invention. Among other things, the occluder assembly 404 includes enclosure top 802, enclosure bottom 810, a first occluder including an occluder blade 813, a shaft 821, a front bracket 819, a rear bracket 817, a bladder 809, and a tube 803, and a second occluder including an occluder blade 814, a shaft 820, a front bracket 818, a rear bracket 816, a bladder 808, and a tube 804. The rear brackets 816 and 817 are mounted to the enclosure top 802 via shaft 825, blocks 826 and 827, and clamps 828 and 829. The rear brackets 816 and 817 are held in a substantially fixed position, although the rear brackets 816 and 817 are able to rotate about the shaft 825 as needed for operation of the occluders. The front bracket 819 is mounted to the enclosure top 802 via shaft 821 and sliding blocks 823 and 824, while the front bracket 818 is mounted to the enclosure top 802 via shaft 820 and sliding blocks 822 and 823. The front brackets 818 and 819 are able to slide forward and backward along channels formed in the sliding blocks 822, 823, and 824 as needed for operation of the occluders. The occluder blades 813 and 814 can be manually retracted if necessary. The edge of the occluder blades 813 and 814 that engages the tubing are typically rounded so as not to cut or crease the tubing.

Chassis Components

The chassis components 414 include various mechanical hardware components that are not considered part of the other assemblies. Among other things, the chassis components 414 include the DC air pump 511, a chassis base, a door sensor (and cable), mounting foot grommets, skins (housing), and associated hardware and fasteners. The housing includes a mounting point, on the back of the unit, for the manual piston bladder (door) vent 503.

Pump Cassette Handling

Figure 11:
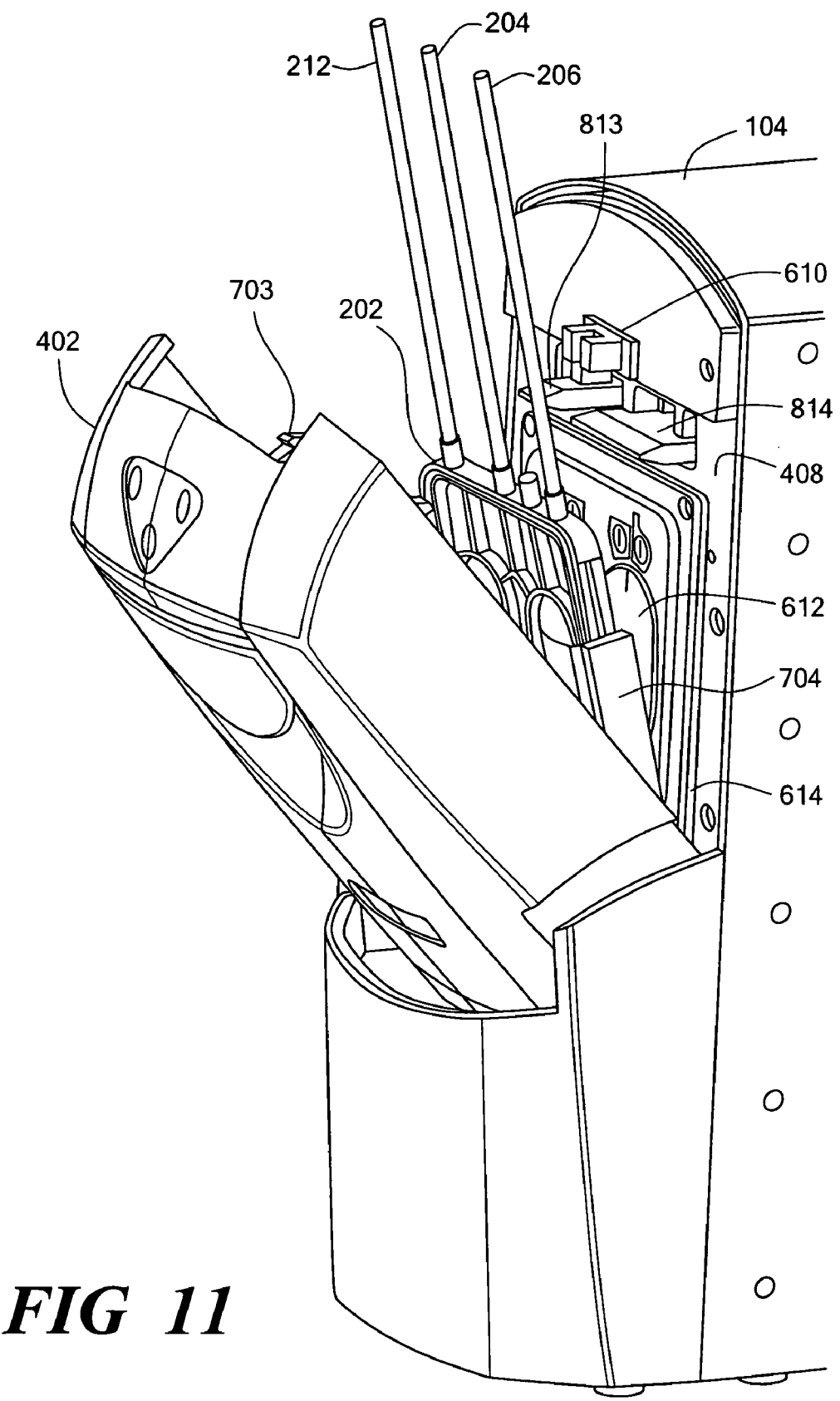
FIG. 11 is a schematic diagram showing the pump cassette installed in the blood pump.

FIG. 11 is a schematic diagram showing the pump cassette 202 installed in the blood pump 104. The pump cassette 202 is installed in the cassette receptacle 704. The door assembly 402 will only close if the pump cassette 202 is oriented correctly in the cassette receptacle 704, and will not close if the pump cassette 202 is inserted backwards so that the tubing connected to the pump cassette 202 does not align with corresponding channels in the door latch 703. When the door assembly 402 is closed and the bladder in the door assembly 402 is inflated, the pump cassette 202 is pressed tightly against the bezel gasket 612 and gasket retainer 614 on the front panel assembly 408, the RBCC inlet tube 204 is captured by the air-in-line sensor 610 on the front plate assembly 408, the occluder blade 813 aligns with and occludes the working solution distribution tube 212, and the occluder blade 814 aligns with and occludes both the RBCC inlet tube 204 and the incubation solution outlet tube 206.

Blood Processing

As discussed above, the compounder 102 and the blood pumps 104 operate under control of the process controller 120. In exemplary embodiments, introduction of the anti-pathogen compound into the RBCC is performed in two stages, a first stage in which the anti-pathogen compound is mixed with buffer solution to a first concentration to form the working solution, and a second stage in which the working solution is mixed with the RBCC to a second concentration to form the incubation solution. The two-stage process is described in more detail in Application D72. A ribbed bezel is preferably used in the blood pumps 104 to limit the amount of working solution that is drawn into the pump cassette during blood processing. Blood processing is described in more detail in Application D71.

The present invention may be embodied in other specific forms without departing from the true scope of the invention. The described embodiments are to be considered in all respects only as illustrative and not restrictive.

What is claimed is:

1. A bezel for use in delivery of pneumatic pressure comprising:
   a rigid block having a pumping side and a port side, the port side having a plurality of ports, each port providing a pneumatic connection to the bezel;
   a plurality of cavities on the pumping side of the rigid block, each cavity in fluid communication through the rigid block with one of the ports;
   at least one depression in the pumping side of the rigid block, the depression having at least two of the plurality of cavities therein; and
   ribs extending up from the depression, the ribs arranged to provide a plurality of air passages between the at least two cavities in the depression; wherein
   the ribs leave an air passage unobstructed by ribs at each of the at least two cavities, such that at each of the at least two cavities the respective air passage connects the cavity to the plurality of air passages between the at least two cavities.

2. A bezel according to claim 1 wherein the ports include hollow tubular structures integral with the rigid block.

3. A bezel according to claim 1 wherein the port side is opposite the pumping side.

4. A bezel according to claim 1 wherein the ports have inner diameters larger in size than the cavities in fluid communication therewith.

5. A bezel according to claim 1 wherein the ribs form a symmetrical grid of air passages.

6. A bezel according to claim 5 wherein the at least one depression includes a chamber wall from which the ribs extend such that removal of the ribs leaves an open chamber defined by the chamber wall.

7. A bezel according to claim 6 wherein the ribs are removable by a milling operation.

8. A bezel according to claim 1 further comprising an open chamber formed by a second depression in the pumping side of the rigid block.

9. A bezel according to claim 8 wherein each of the two depressions includes two of the plurality of cavities therein.

10. A bezel according to claim 1 wherein one or more of the air passages are parallel to a perimeter of the at least one depression.

11. A bezel according to claim 1 wherein the ports are hollow tubular structures integral with the rigid block and extending out from the port side of the block.

12. A bezel according to claim 1 wherein the port side is opposite the pumping side.

13. A bezel according to claim 11 wherein the ports have inner diameters larger in size than the cavity in fluid communication therewith.

14. A bezel according to claim 1 further comprising:
   means for coupling a rib insert in the depression, the rib insert including ribs extending up from the depression to form an elevated contour in the depression, the ribs allowing pneumatic pressure applied through at least one cavity in the depression to be distributed evenly throughout the depression.

15. A bezel for use in delivery of pneumatic pressure comprising:
   a rigid block having a pumping side and a port side, the port side having a plurality of ports, each port providing a pneumatic connection to the bezel;
   a plurality of cavities on the pumping side of the rigid block, each cavity in fluid communication through the rigid block with one of the ports;
   at least one depression in the pumping side of the rigid block, the depression having at least two of the plurality of cavities therein;
   ribs extending up from the depression to form an a plurality of air passages between the at least two cavities in the depression, the ribs allowing pneumatic pressure applied through at least one cavity in the depression to be distributed evenly throughout the depression, wherein;
   the ribs leave an air passage unobstructed by ribs at each of the two cavities, such that at each of the two cavities the respective air passage connects the cavity to the plurality of air passages between the at least two cavities.

16. A bezel according to claim 15 wherein the ribs form a symmetrical grid of air passages.

17. A bezel according to claim 15 wherein the depression includes a chamber wall from which the ribs extend such that removal of the ribs leaves an open chamber defined by the chamber wall.

18. A bezel according to claim 17 wherein the ribs are removable by a milling operation.

19. A bezel according to claim 15 further comprising an open chamber formed by a second depression in the pumping side of the rigid block.

20. A bezel according to claim 19 wherein each of the two depressions includes two of the plurality of cavities therein.

21. A bezel according to claim 15 wherein one or more ribs are parallel to a perimeter of the depression.

22. A bezel according to claim 15 wherein the ports include hollow tubular structures integral with the rigid block.

23. A bezel according to claim 15 wherein the port side is opposite the pumping side.

24. A bezel according to claim 22 wherein the ports have inner diameters larger in size than the cavity in fluid communication therewith.

25. A bezel according to claim 15 wherein each port provides a solvent bondable tubing connection to the bezel.

26. A bezel assembly for use in delivery of pneumatic pressure comprising:
   a rigid block having a pumping side and a port side, the port side having a plurality of ports, each port providing a pneumatic connection to the bezel;
   a plurality of cavities on the pumping side of the rigid block, each cavity in fluid communication through the rigid block with one of the ports;
   at least one depression in the pumping side of the rigid block, the depression having at least two of the plurality of cavities therein; and
   a removable rib insert coupled in the first depression, the rib insert having a plurality of ribs extending up from the depression to form an elevated contour in the depression, the ribs forming a plurality of air passages between the at least two cavities in the depression, and the ribs allowing pneumatic pressure applied through at least one cavity in the depression to be distributed evenly throughout the depression, wherein
   the ribs leave an air passage unobstructed by ribs at each of the two cavities, such that at each of the two cavities the respective air passage connects the cavity to the plurality of air passages between the at least two cavities.

27. A bezel according to claim 26 wherein the ribs form a symmetrical grid of air passages.

28. A bezel according to claim 26 further comprising an open chamber formed by a second depression in the pumping side of the rigid block.

29. A bezel according to claim 28 wherein each of the two depressions includes two of the cavities therein.

30. A bezel according to claim 26 wherein one or more ribs are parallel to a perimeter of the depression.

31. A bezel according to claim 26 wherein the ports include hollow tubular structures integral with the rigid block.

32. A bezel according to claim 26 wherein the port side is opposite the pumping side.

33. A bezel according to claim 31 wherein the ports have inner diameters larger in size than the cavity in fluid communication therewith.

34. A bezel according to claim 26, wherein each port provides a solvent bondable tubing connection to the bezel.

35. A bezel assembly for use in delivery of pneumatic pressure comprising:
a bezel formed by:
a rigid block having a pumping side and a port side, the port side having a plurality of ports, each port providing a pneumatic connection to the bezel;
a plurality of cavities on the pumping side of the rigid block, each cavity in fluid communication through the rigid block with one of the ports;
at least one depression in the pumping side of the rigid block, the depression having at least two of the plurality of cavities therein; and
ribs extending up from the depression, said ribs being arranged to provide a plurality of air passages between the at least two cavities, wherein said ribs leave an air passage unobstructed by ribs at each of the at least two cavities, such that at each of the at least two cavities the respective air passage connects the cavity to the plurality of air passages between the at least two cavities; and
a gasket fitting over the pumping side of the rigid block such that positive pressure applied through the at least one cavity in the depression forces a gasket membrane to move away from the pumping side, and negative pressure applied through the at least one cavity in the depression pulls the gasket membrane against the elevated contour of the ribs.

36. A bezel assembly according to claim 35 wherein the ribs form a symmetrical grid of air passages.

37. A bezel assembly according to claim 35 wherein the depression includes a chamber wall from which the ribs extend such that removal of the ribs leaves an open chamber defined by the chamber wall.

38. A bezel assembly according to claim 37 wherein the ribs are removable by a milling operation.

39. A bezel assembly according to claim 35 further comprising an open chamber formed by a second depression in the pumping side of the rigid block, the second depression having at least one of the cavities therein.

40. A bezel assembly according to claim 39 wherein each of the two depressions includes two of the cavities therein.

41. A bezel assembly according to claim 35 wherein one or more ribs are parallel to a perimeter of the depression.

42. A bezel assembly according to claim 35 wherein the ports include hollow tubular structures integral with the rigid block.

43. A bezel assembly according to claim 35 wherein the port side is opposite the pumping side.

44. A bezel assembly according to claim 35 wherein the ports have inner diameters larger in size than the cavity in fluid communication therewith.

45. A bezel assembly according to claim 35 wherein each port provides a solvent bondable tubing connection to the bezel.

46. A bezel assembly according to claim 35 wherein the ribs are molded into the depression.

47. A bezel assembly according to claim 35 wherein the ribs are inserted into the depression.

48. An assembly for use in the delivery of pneumatic pressure in a medical device comprising:
a rigid block having a pumping side and a port side having a plurality of ports, each port providing a pneumatic connection to the rigid block;
a plurality of cavities on the pumping side of the rigid block, each cavity in fluid communication through the rigid block with one of the ports;
at least one depression in the pumping side of the rigid block, the depression having at least two of the plurality of cavities therein; and
ribs extending up from the depression to form an elevated contour in the depression, the ribs arranged to provide a plurality of air passages between the at least two cavities in the depression; wherein
the ribs leave an air passage unobstructed by ribs at each of the at least two cavities, such that at each of the at least two cavities the respective air passage connects the cavity to the plurality of air passages between the at least two cavities.

49. The assembly according to claim 48 wherein the ports include hollow tubular structures integral with the rigid block.

50. The assembly according to claim 48 wherein the port side is opposite the pumping side.

51. The assembly according to claim 48 wherein the ribs extend up from the depression to form an elevated contour above the pumping side of the rigid block, the ribs allowing pneumatic pressure applied through at least one cavity in the depression to be applied over the elevated contour.

52. The assembly according to claim 48 wherein the ribs form a symmetrical grid of air passages.

53. The assembly according to claim 48 wherein the depression includes a chamber wall from which the ribs extend such that removal of the ribs leaves an open chamber defined by the chamber wall.

54. The assembly according to claim 48 further comprising an open chamber formed by a second depression in the pumping side of the rigid block.

55. The assembly according to claim 54 wherein each of the two depressions includes two of the cavities therein.

* * * * *

UNITED STATES PATENT AND TRADEMARK OFFICE
CERTIFICATE OF CORRECTION

PATENT NO. : 7,632,080 B2
APPLICATION NO. : 10/697450
DATED : December 15, 2009
INVENTOR(S) : Tracey et al.

Page 1 of 1

It is certified that error appears in the above-identified patent and that said Letters Patent is hereby corrected as shown below:

In claim 48, at column 18, line 15, please correct line 15 as follows:

a rigid block having a pumping side and a port side, the port side having

Signed and Sealed this
Twelfth Day of April, 2011

David J. Kappos
*Director of the United States Patent and Trademark Office*